(12) United States Patent
Yoshikawa et al.

(10) Patent No.: US 6,670,119 B1
(45) Date of Patent: Dec. 30, 2003

(54) CANCER-ASSOCIATED GENES

(75) Inventors: Yoshie Yoshikawa, Kyoto (JP);
Hiroyuki Mukai, Moriyama (JP);
Kiyozo Asada, Koga-gun (JP);
Fumitsugu Hino, Kusatsu (JP);
Ikunoshin Kato, Uji (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/377,497

(22) Filed: Aug. 20, 1999

Related U.S. Application Data

(63) Continuation-in-part of application No. PCT/JP98/00667, filed on Feb. 18, 1998.

(30) Foreign Application Priority Data

Feb. 21, 1997 (JP) ............................................. 9-052508

(51) Int. Cl.$^7$ ................................................. C12Q 1/68
(52) U.S. Cl. ...................... 435/6; 536/23.1; 536/23.5; 536/24.3; 530/350
(58) Field of Search .............................. 536/23.1, 23.5, 536/350, 24.3; 435/6; 530/350

(56) References Cited

FOREIGN PATENT DOCUMENTS

| EP | 0 799 892 A2 | 10/1997 |
|---|---|---|
| WO | WO 96/16175 A2 | 5/1996 |
| WO | 96/17080 | 6/1996 |

OTHER PUBLICATIONS

Hillier, L. et al., (XP002220935), Database EMBL Online, database accession No. AA136562, Dec. 10, 1996.
Hillier, L. et al., (XP002220936), Database EMBL Online, database accession No. AA165044, Dec. 21, 1996.
Gattung, S. et al., (XP002220937), Database EMBL Online, database accession No. AC002543, Sep. 20, 1997.
Hillier, L. et al., (XP002220938), Database EMBL Online, database accession No. AA29833, Aug. 20, 1996.
Hillier, L. et al., (XP002220939), Database EMBL Online, database accession No. AA166732, Dec. 21, 1996.
Deadman, R., (XP002220940), Database EMBL Online, database accession No. Z74696, Jun. 25, 1996.
Theopold, U. et al., (XP002220941), Database EMBL Online, database accession No. Z46891, Dec. 6, 1994.
Ulrich Theopold et al., Molecular and Cellular Biology, vol. 15, No. 2, Feb. 1995, XP002220949, pp. 824–834.
Hahn–Jun Lee et al., Biol. Chem., vol. 379, No. 2, Feb. 1998, XP009000928, pp. 175–0183.
Hillier, L. et al., (XP002220942), Database EMBL Online, database accession No. R44840, May 13, 1995.
Hudson, T. et al., (XP002220943), Database EMBL Online, database accession No. G21017, Jun. 1, 1996.
Hillier, L. et al., (XP002220944), Database EMBL Online, database accession No. R40800, May 9, 1995.
Hillier et al., *Database EMBL Online!*, Database Accession No. AA0099387 (XPOO2207188), Oct. 29, 1996.
Hillier et al., *Database EMBL Online!*, Database Accession No. AA0099388 (XPOO2207189), Oct. 29, 1996.
Shiosaka et al., *Br. J. Cancer*, vol. 56, No. 5, 1987, pp. 539–544.
Salesiotis, A.N., et al, Cancer Letters (1995) vol. 91, No. 1, P. 47–54.
Wang, F.L., et al, Cancer Research (1996) vol. 56, No. 16, P. 3634–3637.
Watson, M.A., et al, Cancer Research (1994) vol. 56, No. 17, p. 4598–4602.

*Primary Examiner*—Susan Ungar
*Assistant Examiner*—Minh Tam Davis
(74) *Attorney, Agent, or Firm*—Birch, Stewart, Kolasch & Birch, LLP

(57) ABSTRACT

To provide a method for detecting a cancer cell in a resected specimen by determining a change in an expression level of at least one of cancer-associated genes selected from genes of which cDNA is a DNA comprising a nucleotide sequence as shown in any one of SEQ ID NOs: 1 to 16 and 66 to 68 in Sequence Listing, or a DNA capable of hybridizing with a nucleic acid consisting of a nucleotide sequence as shown in any one of SEQ ID NOs: 1 to 16 and 66 to 68 in Sequence Listing under stringent conditions; as well as a kit for detecting cancer by the above method, and the like.

4 Claims, 3 Drawing Sheets

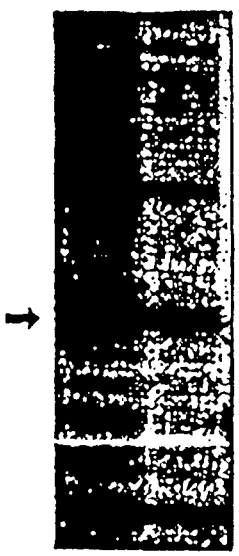
F I G. 1

(a) 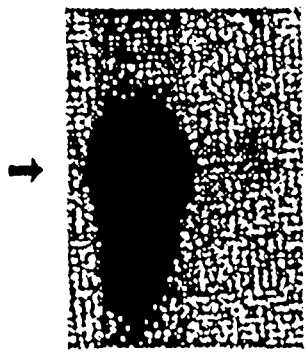
→
(b) 
IN　IT
F I G. 2

CANCER-ASSOCIATED GENES

This application is a continuation-in-part application of PCT/JP98/00667 filed on Feb. 18, 1998, the entire contents of which are incorporated herein by reference.

BACKGROUND OF THE INVENTION

1. Field of the Invention

The present invention relates to a method for detecting a cancer cell characterized by detecting an expression product of a gene capable of changing an expression level thereof owing to canceration. The present invention relates to a gene capable of changing an expression level thereof and a product of the gene owing to canceration.

2. Discussion of the Related Art

Cancers constitute the top of the causes for mortality in Japan since 1981, and a gastric cancer occurs especially at the highest frequency. Recently, there has been known that there is a multi-stage carcinogenic mechanism in the course from a normal cell to a cancer cell [Fearon, E. R. et al., Cell, 61, 759–767 (1990); Sugimura, T., Science, 258, 603–607 (1992)] for which the accumulation of the abnormality in a plurality of genes including DNA repair genes, tumor suppressor genes and oncogenes is essential. Generally, the instability of a gene and the inactivation of a tumor suppressor gene are involved in the development of a cancer, and the activation of an oncogene and/or the overexpression of a growth factor are involved in the advancement and malignancy of a cancer.

The instability of a gene includes the instability of gene associated with abnormality in a DNA mismatch repair system and the instability at a chromosomal level. An example of the former includes the difference in the chain length of a simple repeated sequence present in a genome between a cancer site and a non-cancer site in the same individual (microsatellite instability) [Thibodeau, S. N. et al., Science, 260, 816–819 (1993)], and an example of the latter includes an interchromosomal translocation. The interchromosomal translocation may cause to express a protein which is not found in normal cells, or the interchromosomal translocation may affect an expression level of a protein, even if it is expressed in normal cells. In fact, in human chronic myelocytic leukemia, bcr gene is fused with c-abl gene by the interchromosomal translocation, and there has been confirmed an expression of a hybrid mRNA transcribed from bcr-abl fusion gene, which is absent in normal cells. Further, there has been confirmed that an introduction of bcr-abl fusion gene into an animal results in an onset of leukemia [Watson, J. D. et al., Molecular Biology of Recombinant DNAS, 2nd Ed., Maruzen K. K., 309 (1992)].

The inactivation of a tumor suppressor gene includes, for example, an inactivation of p53 gene. The inactivation is considered to be caused by a deletion within the gene, or a point mutation occurring in a particular portion of an encoding region [Nigro, J. M. et al., Nature, 342, 705–708 (1989); Malkin, D. et al., Science, 250, 1233–1238 (1990)]. In addition, since the deletion and the point mutation of the p53 gene are observed in various cancers, and are as frequent as 60% or higher especially in cases of a gastric cancer at an early stage [Yokozaki, H. et al., Journal of Cancer Research and Clinical Oncology, 119, 67–70 (1992)], the detection of these mutations is considered to be useful for detecting a cancer at an early stage.

On the other hand, p16/MTS1 gene has been known to be a gene which is inactivated owing to a homologous deletion, and high-frequency homologous deletions have been observed in cases of a glioma, a pancreatic cancer and a urinary bladder cancer [Cairns, P. et al., Nature Genetics, 11, 210–212 (1995)]. p16 Protein regulates a cell cycle, and the abnormality in p16 expression has been suggested to be involved in the canceration of a cell [Okamoto, A. et al., Proceedings of the National Academy of Sciences of the United States of America, 91, 11045–11049 (1994)].

As the causation for the activation of an oncogene, there can be included, for example, a viral insertion mutation in a proximity of an oncogene and an interchromosomal translocation. For example, a viral insertion mutation has been confirmed in lymphoma of a chicken which is caused by an avian leukosis virus (ALV). In this case, it has been found that DNA of an ALV is inserted in the proximity of a gene c-myc, and, by potent viral enhancer and promoter, a normal c-myc is overexpressed, and a new sequence which is different partially from the normal gene has been expressed. In addition, in a certain kind of human B cell tumor, there has been confirmed that c-myc, which is one of oncogenes, is located near a potent transcription signal of immunoglobulin by the interchromosomal translocation, whereby increasing its expression level of the mRNA. In this case, no difference has been found between a protein for c-myc in a cancer cell and a protein for c-myc expressed in a normal cell, and the canceration is considered to be caused by an increase in the expression level of the c-myc mRNA [Watson, J. D. et al., Molecular Biology of Recombinant DNAS, 2nd Ed., Maruzen K. K., 305–308 (1992)].

An overexpression of a growth factor includes, for example, an overexpression of C-Met which encodes a hepatocyte growth factor receptor. There has been confirmed that the abnormality in expression of the C-Met is observed as an expression of mRNA having the length of 6.0 kb which is not found in a normal mucous membrane at an early stage of gastric cancer [Kuniyasu, H. et al., International Journal of Cancer, 55, 72–75 (1993)], or is observed at a high frequency, and that a correlation between the gene amplification and the degree of the cancer malignancy is observed [Kuniyasu, H. et al., Biochemical and Biophysical Research Communications, 189, 227–232 (1992)].

As examples of confirming the correlation between the gene abnormality and the degree of cancer malignancy, in addition to that of the c-Met mentioned above, there have been confirmed that an amplification and/or an overexpression of an oncogene C-erbB2 gene is found in mammary cancers, ovarian cancers, gastric cancers and uterine cancers [Wright, C. et al., Cancer Research, 49, 2087–2090 (1989); Saffari, B. et al., Cancer Research, 55, 5693–5698 (1995)]; and that an amplification and/or an overexpression of an oncogene K-sam gene is found in a poorly-differentiated adenocarcinoma which is one tissue type of gastric cancer [Tahara, E. et al., Gastric Cancer, Tokyo, Springer-Verlag, Published in 1993, 209–217], respectively.

As described above, the information concerning the gene involved in the development and the advancement of a cancer as well as the abnormality of such genes has been increasing, and the genetic diagnosis of a biopsy material may serve for an early diagnosis and an assessment of the degree of malignancy of a cancer. However, since a carcinogenic mechanism comprises multiple steps and requires an accumulation of a plurality of mutations, a large part of the genes associated with the canceration have still yet been unknown, and further study is necessary. Recently, a gene therapy in which a normal p53 gene is introduced into a cancer cell whereby suppressing the proliferation of the cancer cell is now at a stage of a clinical trial. Therefore, the solution for a cancer-suppressing gene can shed light not only in the diagnosis but also in the gene therapy.

SUMMARY OF THE INVENTION

Accordingly, a first object of the present invention is to provide a method for detecting cancerated cell and a method for determining a degree of malignancy, on the basis of finding a gene usable as an index for carcinogenesis, particularly a gene capable of changing expression conditions thereof by canceration of a cell, and measuring an expression level of the gene in a resected specimen. A second object of the present invention is to provide a kit used for the above method for detecting a cancer cell and/or a method for determining a degree of malignancy of the cell. A third object of the present invention is to provide a method for controlling proliferation of a cancer cell by using a substance specifically binding to a gene capable of serving as an index for carcinogenesis or an expression product of the gene. Furthermore, a fourth object of the present invention is to provide a novel peptide associated with canceration, and a nucleic acid encoding the peptide. These and other objects of the present invention will be apparent from the following description.

To summarize the present invention, a first invention of the present invention is an invention pertaining to a method for detecting a cancer cell in a resected specimen, characterized by determining a change in an expression level of a gene selected from genes of which cDNA corresponds to a DNA comprising a nucleotide sequence as shown in any one of SEQ ID NOs: 1 to 16 and 66 to 68 in Sequence Listing, or a DNA capable of hybridizing with a nucleic acid as shown in any one of SEQ ID NOs: 1 to 16 and 66 to 68 in Sequence Listing under stringent conditions by, for example, determining a change of an expression level of mRNA or a change of a protein expression level.

A second invention of the present invention is an invention pertaining to a kit for detecting cancer by the method for detecting of the present invention, characterized in that the kit comprises as an essential constituent any one of primers for amplifying mRNA as an index for a change in an expression level, a probe capable of hybridizing with the above mRNA, or an antibody recognizing a protein as an index for the change in expression level.

A third invention of the present invention is a method for controlling proliferation of a cancer cell by using a substance specifically binding to the gene or an expression product thereof, characterized in that cDNA of the gene corresponds to a DNA comprising a nucleotide sequence any one of sequences of SEQ ID NOs: 1 to 16 and 66 to 68 in Sequence Listing, or a DNA capable of hybridizing with DNA as shown in any one of sequences of SEQ ID NOs: 1 to 16 and 66 to 68 in Sequence Listing, wherein the method gives transcriptional control of the gene and/or functional control of an expression product thereof, and the like.

A fourth invention of the present invention is an invention pertaining to a peptide usable for detecting cancer and a nucleic acid encoding the peptide, characterized in that the peptide consists of an amino acid sequence comprising an entire portion of an amino acid sequence as shown in any one of SEQ ID NOs: 17 to 19, 69 and 70 in Sequence Listing or a partial portion thereof and a nucleic acid encoding the peptide.

A fifth invention of the present invention pertains to an antibody usable for detecting cancer, the antibody recognizing the above peptide of the fourth invention.

Incidentally, the term "resected specimen" used in the present specification refers to blood, urine, feces, tissue resected by surgery, and the like. On the other hand, the term "cancer-associated gene" refers to a gene in which the expression conditions thereof change with canceration of a cell.

In order to achieve the objects mentioned above, the present inventors have found a cancer-associated gene by comparing the intracellular expression levels of genes between a cancer tissue and a control normal tissue of a cancer patient, and they have found that cancer cells can be detected by comparing the expression level of this gene. In addition, they have found a novel gene in this cancer-associated gene, whereby completing the present invention.

The terms "cancer tissue" and "control normal tissue" used in the present specification mean a tissue constituting a region of cancerous lesion in a multicellular individual and a tissue constituting a region which is identical spatially to the cancer tissue in the same individual but functions normally.

BRIEF DESCRIPTION OF THE DRAWINGS

FIG. 1 is an autoradiogram showing electrophoretic patterns of the resulting DNA fragment in a case of detecting cancer-associated genes by DD method.

FIG. 2 is an autoradiogram obtained by electrophoresing RNA and then hybridizing a labeled probe with a desired mRNA, in a case of detecting a change in an expression level of mRNA of cancer-associated genes by Northern hybridization method.

DETAILED DESCRIPTION OF THE INVENTION

Figure 3:
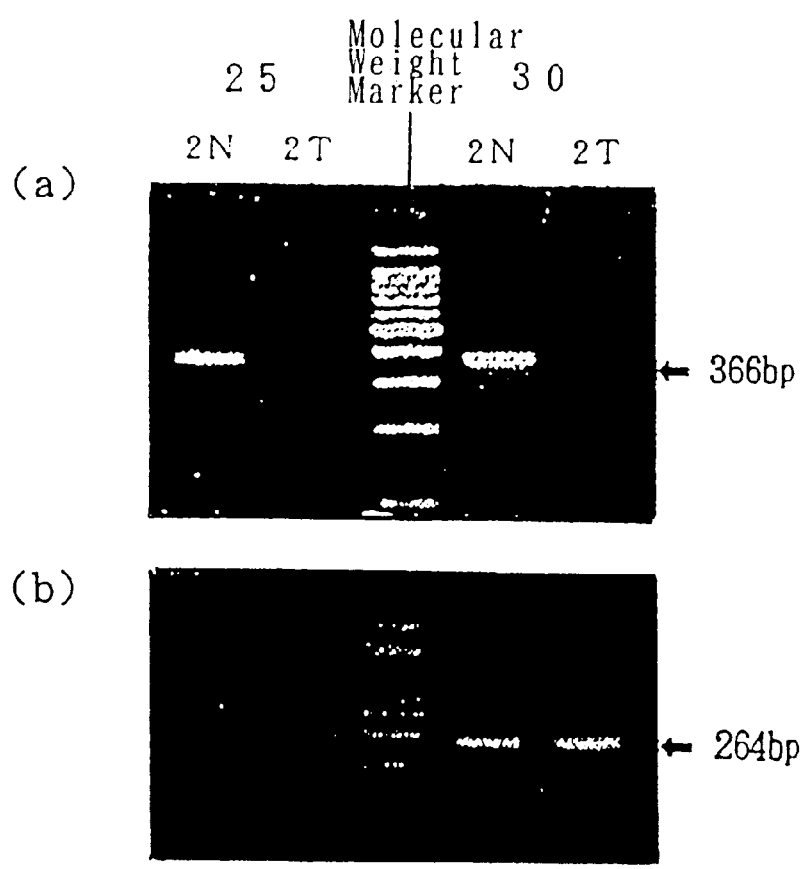
FIG. 3 is a picture showing electrophoretic patterns of the resulting DNA fragment in a case of detecting a change of expression of a cancer-associated gene by RT-PCR method.

The present invention will be explained concretely below.

The first invention of the present invention provides a method for detecting a cancer cell using an expression level of the cancer-associated gene as an index.

A gene which can serve as an index for canceration is a gene capable of changing expression conditions thereof by canceration of a cell, namely, a gene of which expression is significantly induced or suppressed. Such a gene can be detected by, for instance, analyzing copy number of the gene on genome or a pattern for translocation in chromosomes, and comparing an expression level of a gene product in a normal cell and a cancerated cell to identify a gene having differences in both cells. The gene product includes, for example, mRNA transcribed by the above gene or a protein which is a translational product. In the detection in the present invention for a cancer-associated gene, it is efficient to use as an index an expression level of MRNA, in which various methods have been developed for its analysis with the progress in gene manipulation technique. Procedures for confirming a change in an expression level of a gene using as an index an expression level of mRNA includes subtractive hybridization method [Zimmermann, C. R. et al., *Cell*, 21, 709–715 (1989)], Representational Difference Analysis (RDA) method [Lisitsyn, N. et al., *Science*, 259, 946–951 (1993)], molecular index method (Japanese Patent Laid-Open No. Hei 8-322598), Differential Display (DD) method [Liang, P. and Pardee, A. B., *Science*, 257, 967–971 (1992)], and the like. Among them, since the procedures of the DD method are simple, the DD method is suitable for screening a gene in the present invention. The method for screening a cancer-associated gene by using the DD method utilized in the present invention will be described in detail below.

First, mRNA is converted to cDNA by carrying out a reverse transcription reaction with a genome DNA-removed crude RNA sample resulting from treating each RNA individually extracted from a cancer tissue and a control normal tissue to be compared with DNase, together with an oligo (dT) anchor primer and a reverse transcriptase (RTase). Thereafter, the nucleic acid amplification is carried out by polymerase chain reaction (PCR) with the oligo(dT) anchor primer in combination with various random primers.

Subsequently, a PCR-amplified product obtained separately from the tissues to be compared is subjected to polyacrylamide electrophoresis for each amplified product resulting from a combination of an identical primer pair. The band patterns are compared with each other to find a band exhibiting a difference between the normal cell and the cancer cell. This band is cut out from the gel, and a nucleic acid contained in the band is extracted, whereby a DNA fragment which is considered to be complementary to a partial portion with the mRNA for the cancer-associated gene can be obtained.

Thereafter, there is studied whether changes in expression levels of mRNA for the cancer-associated gene can be truly confirmed from the DNA fragment obtained in the DD method described above. When the expression level of the mRNA in a normal tissue is confirmed to be higher than that in the cancer tissue, it is determined that the cancer-associated gene is a gene of which expression level is reduced owing to canceration. On the other hand, when the expression level of the mRNA in the cancer tissue is confirmed to be higher than that in the normal tissue, it is determined that the cancer-associated gene is a gene of which expression level is amplified owing to canceration.

The confirmation on an expression level of mRNA can be made, for example, by labeling the DNA fragment obtained, subjecting a crude RNA sample extracted from either of the cancer tissue or the control normal tissue to Northern hybridization using the above DNA fragment as a detection probe, and confirming the difference in the observed signal intensity with a densitometer. In other words, the stronger the signal intensity, it can be determined that the expression level of the mRNA is high. For example, a signal intensity can be expressed as a value for a volume of a band [IOD (Integrated Optical Density)] obtained from an autoradiogram, or the like. Here, the higher the IOD value, it can be determined that the expression level of the mRNA corresponding to the band is high.

When the expression level of mRNA is too low so that the change in the expression level of the mRNA cannot be confirmed by means of Northern hybridization analysis, there can be also confirmed with more sensitive RNase protection assay [Krieg, P. A. and Melton, D. A., *Methods in Enzymology*, 155, 397–415 (1987)] using as a probe RNA prepared from an amplified DNA fragment obtained by the DD method described above, which is derived from mRNA deduced to be expressed from a cancer-associated gene as a template. This method utilizes RNase having substrate specificity wherein it shows cleaving activity on single-stranded RNA, but shows no cleaving activity on double-stranded RNA. Specifically, an excessive amount of a probe is added to a crude RNA sample extracted from a normal tissue and a cancer tissue-derived crude RNA sample, and the mRNA to be detected forms a hybrid with the added probe, whereby acting on an RNase having substrate specificity. The expression level of the mRNA can be confirmed by determining the amount of the double-stranded RNA remaining after the digestion with the RNase mentioned above. In other words, the larger the amount of the remaining double-stranded RNA, it can be determined that the expression level of the mRNA is high.

The nucleotide sequence of an amplified DNA fragment obtained by the DD method described above, which is derived from mRNA deduced to be expressed from a cancer-associated gene as a template, is sequenced by PCR direct sequencing [Erlich, H. A., *PCR Technology*, Stockton Press, Published in 1989, 45–60], or by a combination of TA cloning [Mead, D. A. et al., *Bio/Technology*, 9, 657–663 (1991)] with a usual nucleotide sequencing method to determine the nucleotide sequence, and the amounts of the amplified product as obtained by carrying out RT-PCR with an amplification primer which is designed based on the above nucleotide sequence information are then compared, whereby the mRNA expression level can be confirmed. In other words, the higher the amount of the resulting amplified product, it can be determined that the expression level of the mRNA is high.

Incidentally, the amplified DNA fragment obtained by the DD method described above, which is derived from mRNA deduced to be expressed from a cancer-associated gene as a template, is not necessarily cDNA complementary to an entire length of mRNA for the cancer-associated gene. In order to obtain cDNA for a cancer-associated gene, for example, a cDNA library derived from a tissue used in screening is prepared; an amplified DNA fragment obtained by the DD method described above, which is derived from mRNA deduced to be expressed from a cancer-associated gene as a template, is labeled; and DNA derived from plaque hybridization is carried out with the labeled cancer-associated gene as a detection probe, whereby cDNA clone for a cancer-associated gene can be isolated.

The present inventors have succeeded in isolating 14 kinds of DNA fragments comprising a respective nucleotide sequence of a partial portion of cDNA for cancer-associated genes. Genes expressing mRNA which corresponds to cDNA as shown in nucleotide sequences comprising a nucleotide for the DNA fragment thus obtained are named as CA11, CA13, CC24, GG24, AG26, GC31, GC32, GC33, GG33, CC34, GC35, GC36, CA42 and CC62, respectively. Correspondences between SEQ ID NOs in Sequence Listing in which a nucleotide sequence of regions presently determined in each nucleotide sequence of cDNA for 14 kinds of cancer-associated genes and the above name of the gene named by the present inventors are shown in Table 1.

TABLE 1

| SEQ ID NOs in Sequence Listing | | |
|---|---|---|
| Nucleotide Sequence | Amino Acid Sequence | Name of Gene |
| 1, 66 | 17, 69 | CA11 |
| 2 | 18 | CA13 |
| 3 | | CC24 |
| 4 | | GG24 |
| 5 | | AG26 |
| 6 | | GC31 |
| 7 | | GC32 |
| 8 | | GC33 |
| 9 | | GG33 |
| 10 | | CC34 |
| 11, 67 | | GC35 |
| 12, 15, 16, 68 | 70 | GC36 |
| 13 | 19 | CA42 |
| 14 | | CC62 |

Here, in Table 1, the nucleotide sequence as shown in SEQ ID NO: 68 comprises the sequences as shown in SEQ ID NOs: 12, 15 and 16. In addition, the amino acid sequence as shown in SEQ ID NO: 70 is a deduced sequence based on the nucleotide sequence as shown in SEQ ID NO: 68.

The above cancer-associated genes are roughly classified into a gene in which the expression level is decreased or increased by canceration. The former genes include CA11, AG26, GC35, GC36 and CC62; and the latter genes include CA13, CC24, GG24, GC31, GC32, GC33, GG33, CC34 and CA42.

By comparing the expression level of each of the genes obtained as above, cancer cells can be detected. In this case, the cancer-associated gene serving as an index may be appropriately selected from the genes listed above, and it may be used as a single kind, or in combination of several kinds of genes. In addition, the cancer-associated gene serving as an index for detection of a cancer cell is not particularly restricted to the 14 kinds of genes listed above, and the cancer-associated gene may be any gene of which cDNA is DNA capable of hybridizing under stringent conditions with the DNA as shown in any one of SEQ ID NOs: 1 to 16 and 66 to 68 in Sequence Listing, as long as the expression level of the gene is changed owing to canceration of a cell.

Conditions capable of hybridizing used in the present specification refer to, for example, those capable of hybridizing by a process comprising incubating DNA immobilized on a nylon membrane with a probe at 65° C. for 20 hours in a solution containing 6×SSC wherein 1×SSC is a solution prepared by dissolving sodium chloride 8.76 g and sodium citrate 4.41 g in 1L of water), 1% SDS, 100 µg/ml herring sperm DNA, 0.1% bovine serum albumin, 0.1% polyvinyl pyrrolidone and 0.1% FICOLL®.

In fact, there has also been confirmed in the present invention the presence of a gene having the characteristics described above. The nucleotide sequence as shown in SEQ ID NO: 10 in Sequence Listing is present in the nucleotide sequence of cDNA for CC34 gene. DNA as shown in this nucleotide sequence wherein T at base number 935 of the sequence is substituted with A, and 6 bases consisting of the sequence of GTTAAG at a 3'-terminal are deleted has been obtained as a DNA fragment with different amplification levels in the DD method using RNA prepared from a normal tissue and RNA prepared from a cancer tissue. This amplified DNA fragment is capable of hybridizing with DNA as shown in SEQ ID NO: 10 in Sequence Listing. Therefore, a gene expressing mRNA which yields this DNA fragment obtained by the DD method in the present invention is also encompassed in the cancer-associated gene for detecting a cancer cell in the present invention.

In addition, as a result of Northern hybridization using highly purified mRNA, it is found that there are plural gene transcriptional products capable of hybridizing with GC36 under stringent conditions, and signals corresponding to each of about 2 kb band, and about 2.4 to about 2.6 kb band are detected in a gastric tissue. In a case of GC35, as a result of Northern hybridization in the same manner as GC36, it is shown that there are plural gene transcriptional products capable of hybridizing with GC35 under stringent conditions and signals corresponding to each of about 1.6 kb; about 3.6 to about 4.0 kb; about 4.5 kb; and about 5.6 to about 6.0 kb are detected in a gastric tissue. It is considered that these mRNAs result from alternative splicing, wherein mRNAs with different sizes are produced by splicing via different combinations of plural exons of primary transcript (mRNA precursor) from the same gene. For instance, a nucleotide sequence of cDNA for nCL-4 encoding digestive tract-specific calpain has high homology with a nucleotide sequence of cDNA for GC36 gene, wherein the nucleotide sequence of cDNA for nCL-4 was clarified at the date after the priority date of the present application [Lee, H.-J. et. al., Biological Chemistry, 379, 175–183, 1998]. In addition, since GC36 gene translation product is identical to nCL-4 except for substitution of one amino acid and deletion of the following 26 amino acids in its amino acid sequence, it is suggested that the mRNA deduced to be expressed from nCL-4 gene and the mRNA deduced to be expressed from GC36 gene are produced by alternative splicing. Further, in the present invention, it is confirmed that an expression level of the mRNA deduced to be expressed from nCL-4 gene is reduced by canceration as in the mRNA deduced to be expressed from GC36 gene. Therefore, the cancer-associated gene usable for detection of cancer cells in the present invention also encompasses mRNAs resulting from alternative splicing, such as the mRNA deduced to be expressed from nCL-4 gene.

The determination of whether or not a cell is a cancer cell is carried out by firstly using a plurality of normal tissues to confirm a normal level of the expression level of the cancer-associated gene used as an index for canceration by a suitable detection method; subsequently determining an expression level of the cancer-associated gene in a resected specimen; and comparing it with the normal level. Specifically, in a case where the expression of the cancer-associated gene as an index is suppressed by canceration, it is determined to be cancer-positive when the expression of this cancer-associated gene cannot be confirmed or can be confirmed only at a level lower than the normal level in a resected specimen. On the contrary, in a case where the expression of the cancer-associated gene as an index is amplified by canceration, it is determined to be cancer-positive when the expression of this cancer-associated gene is at a level higher than the normal level. In the comparison of the expression level of the cancer-associated gene, there may be employed either the amount of mRNA or the amount of a protein expressed from this gene. Incidentally, the normal level referred in the present specification can be shown by the following equation based on the expression level of the cancer-associated gene in a plurality of normal tissues obtained by an appropriate detection method.

[Normal Level Value]=[Mean Expression Level of Cancer-Associated Gene in Normal Tissue]±2×[Standard Deviation]     Equation 1

This normal level value as calculated encompasses 95% of the normal tissues for which the expression level of the cancer-associated gene is determined.

The detection method utilizing mRNA includes, for example, RT-PCR method, RNase protection assay or Northern hybridization.

RT-PCR (Reverse transcribed-Polymerase chain reaction) method refers to a method comprising synthesizing cDNA by reverse transcriptional reaction using mRNA as a template, and thereafter performing nucleic acid amplification by PCR [Kawasaki, E. S. et al., *Amplification of RNA. In PCR Protocol, A Guide to Methods And Applications*, Academic Press, Inc., San Diego, 21–27 (1991)]. In the present invention, nucleic acid amplification reaction is not particularly limited, and may be Strand Displacement Amplification (SDA) method [Walker, G. T., *Nucleic Acids Res.*, 20, 1691–1696 (1992)], Nucleic Acid Sequence-Based Amplification (NASBA) method [Compton, J., *Nature*, 350, 91–92 (1991)], and the like, in which their reaction conditions are also not particularly limited. In addition, the amplified region of cDNA for the cancer-associated gene is not necessarily an entire length of cDNA, but it may be a partial region of the cDNA, as long as the confirmation of the amplified products is not hindered. It is preferable that a primer pair used in nucleic acid amplification reaction is designed so as to specifically amplify only the cDNA. As long as the confirmation of amplified products for the region is not hindered, it does not matter that CDNA which is not subject to detection may be amplified. Incidentally, the term "primer" in the present specification refers to an oligonucleotide capable of acting as an initiation site for DNA synthesis in a case of hybridizing with a template nucleic acid at a suitable temperature under conditions for allowing initiation of synthesis of a primer extension product by DNA polymerase, namely, in the presence of 4 kinds of different nucleotide triphosphates and DNA polymerase in suitable buffer (the buffer being determined by pHs, ionic strength, cofactors, and the like). Typically, the primer comprises 10 to 30 nucleotides. For instance, in a case of CA11 gene in the present specification, there can be exemplified as the former primer a combination of DNAs as shown in SEQ ID NOs: 20 and 21 in Sequence Listing. Hindrance in the confirmation of the amplified products used in the present specification refers, for instance, to a case where the confirmation is carried out by subjecting the amplified DNA fragment to agarose gel electrophoresis, and thereafter staining the gel with ethidium bromide (EtBr), the amount of the amplified DNA fragment present corresponding to mRNA for a cancer-associated gene to be detected cannot be confirmed, since a large number of the amplified DNA fragments having about the same number of bases are produced by nucleic acid amplification reaction, and the separation of each amplified DNA fragment from each other is incomplete.

Amounts of the amplified DNA level can be confirmed by subjecting the nucleic acid amplification reaction mixture to agarose gel electrophoresis; and confirming from the position and the signal intensity of a band detected with a labeled probe capable of specifically hybridizing with a desired amplified fragment. Therefore, the higher the signal intensity obtained by using a certain amount of a crude RNA sample extracted from a resected specimen, it can be determined that the expression level of a cancer-associated gene to be detected is high. The label on the probe is not particularly limited. For example, there can be used a radioactive substance typically exemplified by $^{32}P$, or a fluorescent substance typically exemplified by fluorescein. The signal intensity can, for example, be indicated by IOD of a band on an autoradiogram or a fluorescent image obtained by the method described above.

On the other hand, when an amplified product can be obtained in a sufficient amount, the amplified product can be confirmed by subjecting it to agarose gel electrophoresis, staining the gel with EtBr, and confirming from the position of the amplified DNA fragment and its fluorescent intensity. Therefore, the higher the fluorescent intensity, it can be determined that the expression level of the cancer-associated gene to be detected is high. It is also possible to determine the expression level of the cancer-associated gene from an IOD of a band on a fluorescent image instead of a fluorescent intensity.

In order to carry out a more accurate determination, the degree of amplification needs to be expressed numerically. For example, a quantitative PCR method (Japanese Unexamined Patent Publication No. Hei 5-504886) may be applied in the step of nucleic acid amplification reaction, whereby achieving the purpose mentioned above. A typical method includes adding a known amount of a nucleic acid having at its both terminals the primer nucleotide sequences used in amplification of a desired gene and having different internal sequences and sizes as an internal standard and amplifying by PCR reaction; and deducing the desired gene level by comparing the final amplified level of the desired product in the light of the final amplified level of the internal standard. In the present invention, an internal standard is not limited to an externally added standard, and there may also be used cDNA obtained by using as a template mRNA of a gene expressing in a normal tissue and a cancer tissue in the same level. As such CDNA, for example, there can be included cDNA for β-actin gene which is a constituent of a cell backbone.

For example, in RT-PCR method using a crude RNA sample extracted from gastric cancer tissue cells, when the synthetic oligonucleotides having the nucleotide sequences of SEQ ID NOs: 20 and 21 in Sequence Listing are used as a primer pair for nucleic acid amplification reaction, it is possible to only amplify the nucleotide sequence region as shown in base numbers 122 to 487 in SEQ ID NO: 66 in Sequence Listing of the cDNA nucleotide sequences of a CA11 gene in the present specification as shown in FIG. 3(a).

The expression level of the cancer-associated gene can be determined by RNase protection assay by adding a probe which is RNA in an excess amount capable of specifically hybridizing with mRNA for a cancer-associated gene to be detected or a partial portion thereof to a given amount of a crude RNA sample extracted from a resected specimen, and quantifying the remaining RNA after digestion with the RNase. In other words, the larger the amount of the remaining RNA, it can be determined that the expression level of the cancer-associated gene is high.

Incidentally, a probe used in this method is not particularly limited, as long as it is RNA capable of hybridizing in hybridization buffer, for example, comprising 80% formamide, 40 mM Pipes (pH 6.4), 400 mM NaCl and 1 mM EDTA at 45° C. for 20 hours, and having a nucleotide sequence complementary with a nucleotide sequence specific to mRNA for a cancer-associated gene to be detected. In addition, the label on this probe is not particularly limited, and there may, for example, be used a radioactive substance typically exemplified by $^{32}P$, or a fluorescent substance typically exemplified by fluorescein.

The expression level of the cancer-associated gene can be determined by Northern hybridization by fractionating a given amount of a crude RNA sample extracted from a sample tissue based on the molecular weight; immobilizing on a nylon filter, or the like; bringing mRNA for a cancer-associated gene to be detected into contact with an excess amount of a probe for detecting this gene, and determining the signal intensity obtained from the probe hybridizing with the immobilized RNA. In other words, the higher the signal intensity, it can be determined that the expression level of the cancer-associated gene is high.

Incidentally, the term "hybridizing" used in the method refers, for example, to those capable of hybridizing by a process comprising incubating at 42° C. for 20 hours in hybridization buffer containing 50% formamide, 0.65M NaCl, 0.1M sodium-Pipes, 5×Denhardt's reagent, 0.1% SDS, 5mM EDTA. The detection probe is preferably a nucleic acid having a nucleotide sequence complementary to a nucleotide sequence which is specific to a cancer associated-gene mRNA to be detected. The nucleic acid is not particularly limited, as long as mRNA to be detected can be particularized by location of the above signals, even if its nucleotide sequence is such that signals can be obtained at several spots in the detection of RNA. Labelling of the above probe is not particularly limited, and there can be used, for example, radioactive substances typically exemplified by $^{32}P$, as well as fluorescent substances typically exemplified by fluorescein.

FIG. 2 shows one example of the change in the expression level of mRNA for a cancer-associated gene detected by Northern hybridization method. In this figure, a photograph of an autoradiogram obtained by subjecting each of the RNAs obtained from a cancer tissue and a control normal tissue to electrophoresis individually, and hybridizing with a labeled probe for detecting mRNA for CA11 gene in the present specification.

In addition, when the change in the expression level of a cancer-associated gene is confirmed using a protein as an index, the confirmation may be made based on the biological activity of the protein, and the detection using an antibody against the protein is preferred for its simplicity in the present invention.

The antibody in the present invention is an antibody capable of specifically binding to a protein encoded by the cancer-associated gene. Therefore, the larger the amount of the antibody bound to a given amount of a crude protein extracted from a resected specimen, it can be determined that the expression level of the cancer-associated gene is high.

The protein as an antigen for obtaining the antibody described above can be obtained by purifying from cancer cells expressing the gene, or it can also be obtained by gene engineering technique. For example, a nucleic acid encoding the protein can be obtained by the method described above, in which the DD method is combined with the screening of the cDNA libraries prepared from cells expressing a desired protein. The desired protein can be obtained by incorporating the cDNA obtained into an appropriate expression vector, and expressing it in an appropriate host. Further, this protein may be expressed as a fusion protein. For example, in order to increase the expression level of a desired protein, an appropriate peptide chain is added to the N-terminal or C-terminal derived from other proteins and then allowed to be expressed, and a carrier having an affinity with this peptide chain is used, whereby a desired protein can be purified readily.

In addition, the antigen for obtaining an antibody may not necessarily be an entire molecule of the protein, and the antigen may be a peptide having an amino acid sequence region which is capable of recognizing the antibody and specific to the protein.

As the method for obtaining an antibody, the antibody can, for example, be obtained as an anti-serum by immunizing an animal with a peptide together with an adjuvant by a usual method. Alternatively, it can be obtained as a monoclonal antibody according to the method of Galfre, G. et al [Galfre, G. et al., Nature, 266, 550–552 (1977)].

An example of a method for detecting a protein using an antibody includes Western blotting method.

In this method, the method for detecting with a specific antibody can be carried out by treating cells with a detergent to dissolve intracellular proteins; separating the protein by SDS-polyacrylamide electrophoresis; transferring the resulting protein onto a nitrocellulose membrane, and the like. The antibody bound to a protein can secondarily be detected with, for instance, a $^{125}$I-labeled protein A, a peroxidase-linked anti-IgG antibody, and the like.

The second invention of the present invention provides a kit for detecting a cancer cell. In other words, there can be provided a kit for detecting a cancer cell by utilizing the method for detecting a cancer cell, which is the first invention of the present invention. Concretely, there can be exemplified a kit for detecting the change in the expression level of a cancer-associated gene within the cells using as an index an amount of mRNA or an amount of a protein which is expressed by this gene.

In the case of a kit for detecting a cancer cell using as an index an expression level of mRNA by using the detection method with the nucleic acid amplification described above in connection with the method for detecting a cancer cell, a primer pair is an essential constituent, where the primer pair has the characteristics described above in connection with the method for detecting a cancer cell wherein the primer pair is capable of detecting mRNA of which cDNA is DNA as shown in any one of SEQ ID NOs: 1 to 16 and 66 to 68 in Sequence Listing, or DNA capable of hybridizing under stringent conditions with DNA as shown in a nucleotide sequence comprising the nucleotide sequence as shown in any one of SEQ ID NOs: 1 to 16 and 66 to 68 in Sequence Listing. For example, the kit in the present invention utilizing RT-PCR as a detection method may comprise in addition to the primer pair described above reverse transcriptase, dNTPs and a thermostable DNA polymerase. Incidentally, the kinds and the number of the cancer-associated genes to be detected by this kit are not particularly limited. Therefore, the primer pair constituting this kit is not particularly limited, and it may be selected appropriately depending upon the kinds and the number of the cancer-associated genes to be detected.

One example of the primer pair using as a template cDNA for the cancer-associated gene of the present invention only a part of the region of which is specifically amplified is shown in Table 2. In each primer pair in the table, a symbol of a combination of an alphabet and numerals indicates the name of the primer in the present invention, and a number within a parenthesis attached to each symbol indicates SEQ ID NO: in Sequence Listing showing the nucleotide sequence of each primer. Incidentally, β-actin shown in Table 2 is a gene selected as an internal standard for the purpose of quantifying mRNA for the cancer-associated gene in a crude RNA sample extracted from a resected specimen.

TABLE 2

| Target Gene | | Primer Pair | | Size of Amplified DNA Predicted |
|---|---|---|---|---|
| CA11 | F1 | (20) R1 | (21) | 366 bp |
| CA13 | F2 | (22) R2 | (23) | 168 bp |
| CC24 | F3 | (24) R3 | (25) | 259 bp |
| GG24 | F4 | (26) R4 | (27) | 384 bp |
| AG26 | F5 | (28) R5 | (29) | 389 bp |
| GC31 | F6 | (30) R6 | (31) | 213 bp |
| GC32 | F7 | (32) R7 | (33) | 251 bp |
| GC33 | F8 | (34) R8 | (35) | 563 bp |
| GG33 | F9 | (36) R9 | (37) | 218 bp |
| CC34 | F10 | (38) R10 | (39) | 241 bp |
| GC35 | F11 | (40) R11 | (41) | 157 bp |
| GC36 | F12 | (42) R12 | (43) | 95 bp |
| CA42 | F13 | (44) R13 | (45) | 245 bp |
| CC62 | F14 | (46) R14 | (47) | 134 bp |
| β-Actin | F15 | (48) R15 | (49) | 264 bp |

On the other hand, in the case of a kit for detecting a cancer cell using as an index mRNA by using a detection method employing RNase protection assay or Northern hybridization method, it is an essential requirement for a constituent to have a probe which has the characteristics described above in connection with the method for detecting a cancer and is capable of detecting mRNA of a cancer-associated gene, of which cDNA is DNA comprising the nucleotide sequence as shown in any one of SEQ ID NOs: 1 to 16 and 66 to 68 in Sequence Listing, or DNA capable of hybridizing under stringent conditions with DNA as shown in any one of SEQ ID NOs: 1 to 16 and 66 to 68. For example, in the case of a kit utilizing RNase protection assay, the kit may comprise, in addition to the probe described above, RNase, a concentrated reaction mixture for RNase, and the like. The kinds and the number of the cancer-associated genes to be detected by this kit are not particularly limited. Therefore, a probe constituting this kit is not particularly limited, and it may be selected appropriately depending on the kinds and the number of the cancer-associated genes to be detected.

On the other hand, in the case of a kit for detecting a cancer cell using a protein as an index by using the detection method with an antibody, it is an essential constituent to have an antibody which has the characteristics described above in connection with the method for detecting a cancer cell and is capable of binding individually and specifically to a peptide encoded by DNA as shown in any one of SEQ ID NOs: 1 to 16 and 66 to 68 in Sequence Listing, or DNA as shown in a nucleotide sequence comprising a nucleotide sequence of DNA capable of hybridizing under stringent conditions with DNA as shown in a nucleotide sequence comprising the nucleotide sequence as shown in any one of SEQ ID NOs: 1 to 16 and 66 to 68. The kinds and the number of the cancer-associated genes to be detected by this kit are not particularly limited. Therefore, the antibody constituting this kit is not particularly limited, and it may be selected appropriately depending upon the kinds and the number of the cancer-associated genes to be detected.

By using such a kit, a cancer cell can be detected more simply. Therefore, it is possible to diagnose a cancer based on the determined expression level of a cancer-associated gene by using such a kit. In other words, humans whose confirmation of the presence of the cancer cells is made by the method for detecting a cancer cell using this kit can be determined to be cancer-positive.

The third invention of the present invention is a method for controlling proliferation of a cancer cell using a substance specifically binding to a cancer-associated gene or an expression product thereof. The specific binding substance referred in the present specification can, for example, include nucleic acids, antibodies, cytotoxic T lymphocytes (CTL), and the like.

For example, bcr-abl chimeric protein detected frequently in chronic myelocytic leukemia has a high tyrosine kinase activity and plays an important role in the onset and the proliferation of the leukemia. An antisense oligonucleotide against a gene encoding this chimeric protein can serve to suppress in vivo the proliferation of this gene-expressing tumor (Skorski, T., *Proc. Natl. Acad. Sci. USA* 91, 4504, 1994). On the other hand, a peptide peculiar to a cancer of a protein expressing specifically in a cancer cell has been conventionally known to be a target of T cell immunoresponse to a cancer cell, and a peptide in a proximal site of the fusion of this fusion protein is immunized, whereby obtaining T cells reactive with this fusion protein (Chen, W., *Proc. Natl. Acad. Sci. USA* 89, 1468, 1992), which can, for example, be carried out utilizing the techniques described in the following report. Concretely, CD4+T cells which react specifically with a peptide for ras in which a 12th amino acid glycine is substituted with another amino acid, and which have HLA-DR restrainability are separated in human T cells (Jung, S., *J. Exp. Med.*, 173, 273, 1991); and from a mouse immunized with a recombinant vaccinia virus capable of producing a protein for ras having a mutation in a 61st amino acid a CTL against a peptide consisting of 8 amino acids including such a mutation site can be induced (Skipper, J., *J. Exp. Med.*, 177, 1493, 1993). Further, in a mouse immunized with a solubilized mutated protein for ras prepared by a gene recombination, the proliferation of cancer cells having the same mutation in vivo is suppressed (Fenton, R. G., *J. Natl. Cancer Inst.*, 85, 1294, 1993); and from spleen cells sensitized with a mutated peptide for ras, a CTL exhibiting a cytotoxic activity on cancer cells expressing the same mutated ras is obtained (Peace, D. J., *J. Exp. Med.*, 179, 473, 1994).

Therefore, as to a gene found to be associated with canceration of cells in the present invention, it is possible to control the cell proliferation by using the same antisense oligonucleotide. In addition, if there can be obtained T cells reactive with a protein encoded by a gene of which expression level is considered to be increased owing to canceration, it is possible to suppress the proliferation of cells in which the protein is expressed at a high level.

The fourth invention of the present invention provides a novel peptide usable for the detection of cancer, and a nucleic acid encoding the above peptide. In the cancer associated-gene elucidated by the present inventors, genes except for CA11, CA13, GG33, GC35, GC36 and CA42 have been clarified as genes which have already been isolated and identified by homology search with database in which information of nucleotide sequences is recorded. Specifically, CC24 corresponds to cytochrome c oxidase subunit I gene [Horai, S. et al., *Proc. Natl. Acad. Sci. USA* 92, 532–536 (1995)]; AG26 corresponds to p190-B gene [Burbelo, P. D. et al., *J. Biol. Chem.* 270, 30919–30926 (1995)]; GC31 corresponds to cytochrome c oxidase subunit II gene [Power, M. D. et al., *Nucleic Acids Res.* 17, 6734 (1989)]; GC32 corresponds to cytochrome b gene [Anderson, S. et al., *Nature* 290, 457–465 (1981)]; GC33 corresponds to integrin a 6 subunit gene [Tamura, R. N. et al., *Journal of Cell Biology*, 111, 1593–1604 (1990)]; GG24 corresponds to F1-ATPase β subunit gene [Ohta, S. et al., *The Journal of Biochemistry*, 99, 135–141 (1986)]; and CC62 corresponds to lactoferrin gene [Rey, M. W. et al., *Nucleic Acids Res.* 18, 5288 (1990)]. On the other hand, CC34 cDNA clone is a clone different from a partial region of the cDNA nucleotide sequence encoding 16SrRNA [Horai, S. et al., *Proc. Natl. Acad. Sci. USA* 92, 532–536 (1995)] by 7 bases. Incidentally, the association with carcinogenesis for these genes has not been known.

On the other hand, as to each of the genes of CA11, CA13, GG33, GC35 and CA42, no reports have been yet made with regard to the nucleotide sequence, the sequence identical to the amino acid sequence encoded therein or the sequence having a homology therewith in the region analyzed herein in each of cDNAs for the genes. As a result of additional analysis, it is clarified that a nucleotide sequence of cDNA for GC36 gene has homology with a nucleotide sequence of cDNA for nCL-4 as mentioned above. Here, the cDNA for nCL-4 has a nucleotide sequence, wherein 78 bp of bases are inserted between base numbers 956 and 957 of SEQ ID NO: 68 in Sequence Listing, and 241 bp at 3'-terminal of bases are deleted. Namely, GC36 cDNA sequence is different from nCL-4 cDNA sequence. In other words, in the nucleotide sequence of each of cDNAs for the genes of CA11, CA13, GG33, GC35, GC36 and CA42, a nucleic acid having the nucleotide sequence clarified in the present invention is a novel nucleic acid isolated for the first time by the present inventors.

As shown in Table 1, a peptide encoded by a novel nucleic acid in the present invention comprising the nucleotide sequence as shown in each of SEQ ID NOs: 66, 2, 13 and 68 in Sequence Listing is deduced based on this nucleotide sequence that the peptide comprises the amino acid sequence as shown in each of SEQ ID NOs: 69, 18, 19 and 70 in Sequence Listing, without being limited thereto. Specifically, there also are encompassed [1] a peptide comprising an entire portion of the amino acid sequence as shown in any one of SEQ ID NOs: 17 to 19, 69 and 70 in Sequence Listing, or a partial portion thereof; and [2] a peptide resulting from addition, deletion or substitution of one or more amino acids in the amino acid sequence as shown in any one of SEQ ID NOs: 17 to 19, 69 and 70 in Sequence Listing, and having a change in the expression level owing to canceration of cells, because of the reasons described below.

In a naturally-occurring protein, mutations such as deletion, insertion, addition and substitution of amino acids can take place in its amino acid sequence in addition to a polymorphism or a mutation in a gene encoding it as well as a modification in vivo or in purification step after its production. Nevertheless, when such a mutation is present in a region in which it is insignificant to preserve the activities and the structure of the protein, there have been known to exhibit physiological and biological activities substantially of the same level as those of the proteins without mutations.

In addition, the same can be said for the case where the mutations described above are artificially introduced into an amino acid sequence of the protein, in which case diversified, various kinds of mutants can be further prepared. For instance, it has been also known that a polypeptide resulting from substitution of a particular cysteine residue with serine in the amino acid sequence of human interleukin 2 (IL-2) retains IL-2 activity [Wang, A. et. al., *Science*, 224, 1431–1433 (1984)]. Therefore, proteins are encompassed within the scope of the present invention, as long as no difference in the change in an expression level owing to canceration is found, even if the protein has an amino acid sequence which results from deletion, insertion, addition or substitution of one or several amino acid residues in an amino acid sequence disclosed by the present invention.

Further, certain kinds of proteins have been known to have a peptide region which is unessential for its activity. Examples are signal peptide present in a protein secreted extracellularly, and a pro-sequence found in a precursor of a protease, or the like, and almost all of these regions are removed after translation or when converted into an active protein. Such proteins are present in the form of different primary structures, but the proteins exhibit equivalent functions eventually.

When a protein is produced by a gene engineering technique, a peptide chain irrelevant to the activity of a desired protein may be added to an amino terminal or carboxyl terminal of the protein. For example, in order to increase the expression level of a desired protein, a fusion protein resulting from adding a part of an amino terminal region of a protein highly expressed in a host used to an amino terminal of a desired protein may be prepared. Alternatively, in order to facilitate the purification of the protein expressed, a peptide having an affinity with a particular substance may be added to an amino terminal or carboxyl terminal of a desired protein. These added peptides may remain in an added state when there is no adverse effect on the activity of a desired protein, or the added peptides may be removed from a desired protein, if necessary, by means of an appropriate treatment such as a limited degradation with a protease.

Even a protein having or adding a peptide unessential for its function is also encompassed within the scope of the protein of the present invention, as long as it can exhibit an equivalent function. The term "peptide" in the present specification refers to two or more amino acids bound to each other via peptide bonds, and is intended to encompass those referred to as "protein."

A partial portion of the novel nucleic acid in the present invention consists of a nucleic acid encoding a peptide having the amino acid sequence as shown in any one of SEQ ID NOs: 17 to 19, 69 and 70 in Sequence Listing, wherein its nucleotide sequence include those as shown in Table 1, for instance, the nucleotide sequence as shown in any one of SEQ ID NOs: 1, 2, 13, 66 and 68 and in Sequence Listing. In other words, the peptide having the amino acid sequence as shown in SEQ ID NO: 17 in Sequence Listing is encoded by the base numbers 2 to 598 of the nucleotide sequence as shown in SEQ ID NO: 1 in Sequence Listing; the peptide having the amino acid sequence as shown in SEQ ID NO: 69 in Sequence Listing is encoded by the base numbers 64 to 660 of the nucleotide sequence as shown in SEQ ID NO: 66 in Sequence Listing; the peptide having the amino acid sequence as shown in SEQ ID NO: 18 in Sequence Listing is encoded by the base numbers 1698 to 1850 of the nucleotide sequence as shown in SEQ ID NO: 2 in Sequence Listing; the peptide having the amino acid sequence as shown in SEQ ID NO: 70 in Sequence Listing is encoded by base numbers 83 to 2074 of the nucleotide sequence as shown in SEQ ID NO: 68; the peptide having the amino acid sequence as shown in SEQ ID NO: 19 in Sequence Listing is encoded by the base numbers 8 to 196 of the nucleotide sequence as shown in SEQ ID NO: 13 in Sequence Listing, respectively, but the nucleic acids encoding the novel peptide in the present invention are not limited thereto. Specifically, there are also encompassed within the present invention 1) a nucleic acid encoding a peptide usable for detection of a cancer cell, wherein the peptide comprises an entire sequence of the amino acid sequence as shown in any one of SEQ ID NOs: 17 to 19, 69 and 70 in Sequence Listing, or a partial sequence thereof; 2) a nucleic acid encoding a peptide capable of changing its expression level owing to canceration of a cell, wherein the nucleic acid is capable of hybridizing with the novel nucleic acid of the present invention under stringent conditions; 3) a nucleic acid encoding a peptide usable for detection of a cancer cell by the change in its expression level, wherein one or more amino acids are added, deleted or substituted in the amino acid sequence as shown in any one of SEQ ID NOs: 17 to 19, 69 and 70 in Sequence Listing, and the like.

The term "nucleic acid encoding an amino acid sequence" described in the present specification will be described. There has been known that as the codon (triplet base combination) designating a particular amino acid on a gene, 1 to 6 kinds each exist for every amino acid. Therefore, there can be a large number of nucleic acids each encoding an amino acid sequence, depending on its amino acid sequence. In nature, the gene does not exist in a stable form, and it is not rare that the mutation of its nucleotide sequence takes place. The mutation on the gene may not affect the amino acid sequence to be encoded (so-called "silent mutation"), in which case it can be said that different nucleic acids encoding the same amino acid sequence have been produced. There cannot, therefore, be denied the possibility that even when the nucleic acid encoding a particular amino acid sequence is isolated, a variety of nucleic acids encoding the same amino acid sequence are produced with generation passage of the organism containing them. Moreover, it is not difficult to artificially produce a variety of the nucleic acids encoding the same amino acid sequence by means of various genetic engineering techniques. For example, when a codon used on a natural nucleic acid encoding the desired protein is low in usage in the host in the production of a protein by genetic engineering, the expression level of the protein is sometimes insufficient. In such a case, high expression of the desired protein is achieved by artificially converting the codon into another one of commonly used in the host without changing the amino acid sequence encoded (for example, Japanese Examined Patent Publication No. Hei 7-102146). It is of course possible to artificially produce a variety of nucleic acids encoding a particular amino acid sequence, and the nucleic acids can be also produced in nature. Therefore, the present invention includes a nucleic acid, as long as the nucleic acid encodes an amino acid sequence disclosed in the present specification, even if it is not a nucleic acid having same nucleotide sequence disclosed in the present specification.

In fact, in the present invention, nucleic acids of which nucleotide sequences are slightly different but the amino acid sequence encoded is identical is obtained. Although R at base number 1784 is A, and K at base number 1985 is T in the nucleotide sequence as shown in SEQ ID NO: 2 in Sequence Listing of which the nucleotide sequence is contained in a nucleotide sequence for cDNA of CA13 gene, there is obtained cDNA in which R at base number 1784 is G, and K at base number 1985 is T; and a nucleic acid in which R at base number 1784 is A, and K at base number 1985 is G in the nucleotide sequence as shown in SEQ ID NO: 2 in Sequence Listing. However, the differences of the nucleotide sequence at these two sites do not affect the amino acid sequence encoded in base numbers 1698 to 1850 in the nucleotide sequence as shown in SEQ ID NO: 2 in Sequence Listing, and each peptide encoded by the above three kinds of nucleic acids has the amino acid sequence as shown in SEQ ID NO: 18 in Sequence Listing.

Among the cDNAs for novel genes of the present invention, CDNA for CA11 gene has the nucleotide sequence as shown in SEQ ID NOs: 1 and 66; CDNA for CA13 gene has the nucleotide sequence as shown in SEQ ID NO: 2; CDNA for GG33 gene has the nucleotide sequence as shown in SEQ ID NO: 9; cDNA for GC35 gene has the nucleotide sequences as shown in SEQ ID NOs: 11 and 67; cDNA for GC36 gene has the nucleotide sequences as shown in SEQ ID NOs: 12, 15, 16 and 68; and cDNA for CA42 gene has the nucleotide sequences as shown in SEQ ID NO: 13. Here, the nucleotide sequence as shown in SEQ ID NO: 66 comprises the nucleotide sequences as shown in SEQ ID NO: 1; the nucleotide sequence as shown in SEQ ID NO: 67 comprises the nucleotide sequences as shown in SEQ ID NO: 11; and the nucleotide sequence as shown in SEQ ID NO: 68 comprises the nucleotide sequences as shown in SEQ ID NOs: 12, 15 and 16.

Moreover, the novel nucleic acids of the present invention include a nucleic acid capable of hybridizing with the nucleic acid having the nucleotide sequences as shown in any one of SEQ ID NOs: 66, 2, 9, 67, 13 as well as 68 in Sequence Listing under stringent conditions, wherein the nucleic acid is complementary to a nucleotide sequence for mRNA capable of changing an expression level by canceration. In fact, the nucleic acid having the above properties is obtained in the present invention. For instance, there are obtained the above nucleic acid of which nucleotide sequence is slightly different but an encoded amino acid sequence is identical.

In addition, the fifth invention of the present invention provides an antibody against the peptide encoded by the novel nucleic acid in the present invention. The above antibody can be utilized for detection of the cancer cell described above.

EXAMPLES

The present invention will be described more concretely hereinbelow by means of the working examples, without intending to restrict the scope of the present invention thereto.

Example 1

Analysis of Cancer-Associated Gene

1) Confirmation of mRNA Which Can Serve As Index for Detecting Cancer

There was confirmed whether or not mRNA of which expression level was changed by canceration was present by DD method comprising comparing the expression of mRNA of a cancerated lesion tissue with that of a control normal tissue of a stomach as detailed below.

First, from each of a cancer tissue and a control normal tissue of a stomach excised from a patient with an advanced, poorly-differentiated adenocarcinoma, RNA was extracted with TRIZOL™ reagent (manufactured by Gibco BRL) to obtain a crude RNA sample. A 50 µg portion of the crude RNA sample thus obtained was reacted with 10 units of DNaseI (manufactured by Takara Shuzo Co., Ltd.) at 37° C. for 30 minutes in the presence of 5 mM $MgCl_2$ as a final concentration and 20 units of RNase inhibitor (manufactured by Takara Shuzo Co., Ltd.) to remove genomic DNA. Using this RNA, RT-PCR was carried out with DIFFERENTIAL DISPLAY™Kit (manufactured by Display Systems) and Enzyme Set-DD (manufactured by Takara Shuzo Co., Ltd.) in accordance with the procedures described in the instruction attached to the kit.

Specifically, reverse transcription reaction was carried out per one reaction by mixing 200 ng of the crude RNA sample treated with the above DNase, and any one kind of the oligonucleotides having the nucleotide sequences as shown in SEQ ID NOs: 56 to 64 in Sequence Listing as a primer, thereafter heat-treating at 70° C. for 10 minutes, subjecting to rapid cooling, and subsequently reacting with AMV reverse transcriptase at 55° C. for 30 minutes. Other downstream primers were individually reacted in the same manner to prepare 9 kinds of single-stranded cDNA samples in total.

In the subsequent nucleic acid amplification reaction by PCR, a nucleic acid amplification was carried out by PCR using each of the 9 kinds of single-stranded cDNAs described above as a template, an oligo(dT) primer identical to that used in the reverse transcription as a downstream primer, and any one kind of the 10 mer-oligonucleotides in the kit which had the nucleotide sequences as shown in SEQ ID NOs: 50 to 55 in Sequence Listing as an upstream primer, to prepare 54 kinds of amplified DNA samples in total.

The PCR was carried out by adding 3 mM $MgCl_2$, 15 µM each of dATP, dGTP, dCTP and dTTP as substrates, and 1.85 kBq/ml [α-$^{33}$P]-dATP (manufactured by Amersham) as a labelling compound, and reacting for 40 cycles, wherein one cycle consists of at 94° C. for 30 seconds, at 40° C. for 60 seconds and at 72° C. for 60 seconds. After termination of the reaction, an equivolume of 95% formamide was added, and the mixture was subjected to thermal denaturation at 90° C. for 2 minutes to obtain a sample for electrophoresis. The electrophoresis was carried out on a 7 M urea-denatured 5% polyacrylamide gel, and autoradiography yielded a fingerprint comprising a large number of bands, wherein there were found to be bands having different signal intensities between the autoradiogram of the cancer tissue and that of the control normal tissue.

As one example, the results where D4 having the nucleotide sequence as shown in SEQ ID NO: 59 in Sequence Listing was used as a downstream primer, and U1 having the nucleotide sequence as shown in SEQ ID NO: 50 was used as an upstream primer are shown in FIG. 1. Specifically, FIG. 1 is a reproduced photograph of an autoradiogram showing electrophoretic patterns of the DNA fragment obtained when a cancer-associated gene was detected by the DD method. Here, in FIG. 1, 1N is a lane wherein on an acrylamide gel was electrophoresed an amplified DNA fragment obtained by using as a template a crude RNA sample obtained from a normal tissue of a patient with a poorly-differentiated adenocarcinoma-type gastric cancer; and 1T is a lane wherein on an acrylamide gel was electrophoresed an amplified DNA fragment obtained by using as a template a crude RNA sample obtained from a cancer tissue of the same patient with the poorly-differentiated adenocarcinoma-type gastric cancer, respectively. A band having a stronger signal intensity in the autoradiogram obtained from the control normal tissue than in the autoradiogram of the cancer tissue sample was found at the position corresponding to about 750 bp as indicated with "→" in FIG. 1. The present inventors named the gene expressing the mRNA which causes the band to show this difference in the intensity as CA11.

Table 3 showed the combination of the upstream and downstream primers for detecting the difference in the expression level of each mRNAs by means of the DD method, an the approximate size of an amplified DNA fragment, and the difference in the level of the amplified DNA obtained by RT-PCR from the cancer tissue and the control normal tissue for each of genes which was detected by the present inventors with the DD method and named. In the column of the primers in Table 3, a symbol of a combination of an alphabet and numerals indicates the name of a primer, and a number within a parenthesis attached to each symbol indicates SEQ ID NO: showing the nucleotide sequence of the primer in Sequence Listing.

TABLE 3

| Name of Gene | Primer Pair Up-stream | Down stream | Approximate Size of Amplified DNA fragment | Difference in Amount of DNA fragment |
| --- | --- | --- | --- | --- |
| CA11 | U1 (50) | D4 (59) | 750 bp | Cancer Tissue < Normal Tissue |
| CA13 | U1 (50) | D4 (59) | 620 bp | Cancer Tissue > Normal Tissue |
| CC24 | U2 (51) | D5 (60) | 800 bp | Cancer Tissue > Normal Tissue |
| GG24 | U2 (51) | D9 (64) | 480 bp | Cancer Tissue > Normal Tissue |
| AG26 | U2 (51) | D3 (58) | 550 bp | Cancer Tissue < Normal Tissue |
| GC31 | U3 (52) | D8 (63) | 440 bp | Cancer Tissue > Normal Tissue |
| GC32 | U3 (52) | D8 (63) | 310 bp | Cancer Tissue > Normal Tissue |
| GC33 | U3 (52) | D8 (63) | 300 bp | Cancer Tissue > Normal Tissue |
| GG33 | U3 (52) | D9 (64) | 410 bp | Cancer Tissue > Normal Tissue |
| CC34 | U3 (52) | D5 (60) | 290 bp | Cancer Tissue > Normal Tissue |
| GC35 | U3 (52) | D8 (63) | 210 bp | Cancer Tissue < Normal Tissue |
| GC36 | U3 (52) | D8 (63) | 190 bp | Cancer Tissue < Normal Tissue |
| CA42 | U4 (53) | D4 (59) | 660 bp | Cancer Tissue > Normal Tissue |
| CC62 | U6 (55) | D5 (60) | 380 bp | Cancer Tissue < Normal Tissue |

2) Identification of mRNA Serving as Index for Detecting Cancer

There was investigated whether a change in an expression level of the mRNA used as a template for an amplified DNA fragment derived from each of the genes shown in Table 3 as confirmed by the DD method in Section 1) described above was truly associated with canceration.

First, the studies were made by means of Northern hybridization. Specifically, there was studied whether the difference in the expression levels of the mRNA of a cancer-associated gene expressed in a cancer tissue and that in a control normal tissue could be detected by using each amplified DNA fragment obtained by the method in Section 1) described above as a probe.

The probe for the detection was prepared as follows. Specifically, from the acrylamide gel on which the amplified DNA fragment obtained by the DD method in Section 1) described above was electrophoresed, the region containing each amplified DNA fragment shown in Table 3 was cut out, and thereto was added 100 μl of water and subjected to a heat extraction to collect individually each DNA fragment contained. Re-amplification by PCR was carried out by using each DNA fragment individually as a template, with a combination of the upstream and downstream primers used to obtain each DNA fragment shown in Table 3. Further, about 100 ng of each amplified DNA fragment was labeled with 32p using Random Primer DNA Labeling Kit (manufactured by Takara Shuzo Co., Ltd.) to prepare 14 kinds of probes for detection. Separately from above, mRNA for β-actin gene was selected as a positive control of a crude RNA extracted from each tissue, and the synthetic oligonucleotide having the nucleotide sequence as shown in SEQ ID NO: 65 in Sequence Listing was labeled in the same manner with $^{32}$P to obtain a probe for detecting mRNA for β-actin gene. Thereafter, the probe for detection described above was mixed together with herring sperm DNA so as to have a concentration of 100 μg/ml, and then heat-denatured. To the resulting reaction mixture was added hybridization buffer (50% formamide, 0.65 M NaCl, 0.1M Na-Pipes, 5×Denhardt's reagent, 0.1% SDS, 5 mM EDTA) to prepare 15 kinds of probe solutions for detection in Northern hybridization.

Northern hybridization was carried out as follows. First, 20 μg per well of a crude RNA sample extracted from each of a cancer tissue and a control normal tissue from the patient with a gastric cancer prepared as described above was subjected to electrophoresis on a formalin-denatured 1% agarose gel and blotted on a Hybond N$^+$ membrane (manufactured by Amersham). Subsequently, a blotted membrane and hybridization buffer added with heat-denatured herring sperm DNA so as to have final concentration of 100 μg/ml were added to a Hybri Bag (manufactured by COSMO BIO). The resulting composition was allowed to stand at 42° C. for 2 hours, and then the buffer was discarded to prepare a membrane with pre-hybridization treatment. After preparing 15 such membranes as above, to each membrane was added each of the 15 kinds of detection probe solutions for Northern hybridization described above, and hybridization was carried out at 42° C. for 16 hours. Thereafter, each blotted membrane was taken from the Hybri Bag, and rinsed with washing solution I (2×SSC, 0.2% sodium pyrophosphate, 0.1% SDS) at 42° C. for 20 minutes, and then with washing solution II (0.5×SSC, 0.2% sodium pyrophosphate, 0.1% SDS) at 42° C. for 20 minutes. Incidentally, rinsing with washing solution II was repeated twice with replacing the washing solution. The membrane after rinsing was wrapped with a plastic film and exposed for one day and night to a high-sensitivity X-ray film (manufactured by Kodak). From the signal intensity in the resultant autoradiogram, the expression level in the cancer tissue was compared with that of the control normal tissue.

As one example, the results of the detection of mRNA for CA11 gene are shown in FIG. 2. In FIG. 2, 1N is a lane wherein on an agarose gel was electrophoresed a crude RNA sample obtained from a normal tissue of a patient with a poorly-differentiated adenocarcinoma-type gastric cancer; and 1T is a lane wherein on an agarose gel was electrophoresed a crude RNA sample obtained from a cancer tissue of the same patient with the poorly-differentiated adenocarcinoma-type gastric cancer. (a) shows results obtained with a probe for detecting CA11, and (b) shows results obtained with a probe for detecting β-actin. Since both of the 1N and the 1T exhibited the signals obtained with the probes for detecting β-actin as shown in (b), it is clear that in the both samples the RNA is extracted without undergoing degradation excessively. On the other hand, a clear signal as indicated by "→" at a position near 1.1 kb was present only in lane 1N but no signals were present in lane 1T as shown in (a). Therefore, it was found that the CA11 was a gene of which expression level was reduced owing to canceration. Similarly, CC62 exhibited a band at about 2.6 kb only on the autoradiogram derived from the control normal stomach tissue. GC31, GC32 and CC34 showed the bands at about 1.0 kb, about 1.6 kb and about 1.7 kb, respectively, and in any of these genes more intensive signal was obtained for the crude RNA samples prepared from the gastric cancer tissues as compared to that of the crude RNA samples prepared from the control normal stomach tissues. Incidentally, the signal intensity was determined by measuring each band of an autoradiogram by a densitometer. Subsequently, IOD of each band obtained on the autoradiogram was calculated with FMBIO-100 (manufactured by Hitachi Soft Engineering), and an index was calculated by the equation as shown below to determine whether or not a gene was a cancer-associated gene.

$$[\text{Index Value}] = (X \times \beta Y)/(Y \times \beta X) \quad \text{Equation 2}$$

In the above equation, each symbol expresses the following value:

X: IOD of a band derived from mRNA for the gene shown in Table 3 obtained from a gastric cancer tissue;

Y: IOD of a band derived from mRNA for the gene shown in Table 3 obtained from a control normal stomach tissue;

βX: IOD of a band derived from mRNA for β-actin gene obtained from a gastric cancer tissue; and βY: IOD of a band derived from mRNA for β-actin gene obtained from a control normal stomach tissue.

The comparison on the expression level was made by carrying out RT-PCR with respect to each of the genes CA13, CC24, GG24, AG26, GC33, GG33, GC35, GC36 and CA42 in which no signals were obtained by Northern hybridization. In order to design a primer for the nucleic acid amplification action in the RT-PCR, each DNA fragment used as a probe in Northern hybridization was subjected to a direct sequencing by PCR, or was cloned by a TA cloning procedure and then sequenced by a dideoxy method, whereby determining its nucleotide sequence. The nucleotide sequences of primers designed based on the resulting nucleotide sequence information and used in the RT-PCR with mRNA derived from each of the genes as a template are as shown in any of SEQ ID NOs: 22 to 29, 34 to 37 and 40 to 45 in Sequence Listing. Table 2 shows the genes together with the corresponding primers used to confirm their expression.

A change in an expression level of mRNA by RT-PCR was confirmed by a DNaseI treatment of a crude RNA sample obtained from each of the cancer tissue and the control normal tissue of a patient with a gastric cancer prepared by the method in Section 1) described above. Thereafter, RT-PCR was carried out in a 100 μl reaction system of 40 ng of each treated sample with TaKaRa RNA PCR Kit Ver. 2.1 according to the procedures described in the instruction attached to the kit. Specifically, 40 ng of a crude RNA sample as a template and an oligo(dT) primer (final concentration: 2.5 μM) as a downstream primer were used to prepare a reverse transcription reaction mixture (10 mM Tris-HCl, pH 8.3, 50 mM KCl, 5 mM MgCl$_2$, 1 mM each of dNTPs, 100 units of RNase inhibitor, 25 units of AMV reverse transcriptase), and the reverse transcription reaction was carried out at 30° C. for 10 minutes, and at 55° C. for 20 minutes and then at 95° C. for 5 minutes. Each 10 μl of the reverse transcription reaction mixture was added to each 40 μl of 10 kinds of PCR reaction mixtures (final concentration: 10 mM Tris-HCl, pH 8.3, 50 mM KCl, 2.5 mM MgCl$_2$, 1.25 units of TaKaRa Taq DNA polymerase) individually containing the primer pairs (0.2 μM) for detecting each of the mRNAs for the genes of CA13, CC24, GG24, AG26, GC33, GG33, GC35, GC36, CA42 and v-actin to make up a volume of 50 pl. One cycle after the pre-incubation at 94° C. for 2 minutes in PCR consisted of the step of incubation at 94° C. for 30 seconds, at 55° C. for 60 seconds, and then at 72° C. for 60 seconds. The amount of an amplified DNA product was quantified by subjecting the amplified DNA product to agarose gel electrophoresis, staining the gel with ethidium bromide, calculating the IOD of each band on the fluorescent image with FMBIO-100 to obtain an index for determining whether or not a gene is a cancer-associated gene from Equation 2 shown above.

The results of Northern hybridization method and RT-PCR described above, and the patterns of the changes in the expression owing to the canceration of each of the genes evident from these results were shown in Table 4. In the column of the patterns of the changes in the expression, a gene of which expression was amplified owing to canceration was indicated with "↑" and a gene of which expression was suppressed owing to canceration was indicated with "↓". Specifically, it was determined in Table 4 that a gene having an index value greater than 1 is a gene of which expression level was increased owing to canceration, and a gene having an index value less than 1 is a gene of which expression level was reduced owing to canceration. As a result, there were clarified that the genes CA13, CC24, GG24, GC31, GC32, GC33, GG33, CC34 and CA42 were those of which expression levels were increased owing to canceration, and the genes CA11, AG26, GC35, GC36 and CC62 were those of which expression levels were reduced owing to canceration.

TABLE 4

| Name of Gene | Index Value | Method for Determining Index Value | Patterns of Changes in Expression |
| --- | --- | --- | --- |
| CA11 | 0.036 | A | ↓ |
| CA13 | 6.3 | B | ↑ |
| CC24 | 2.0 | B | ↑ |
| GG24 | 2.8 | B | ↑ |
| AG26 | 0.52 | B | ↓ |
| GC31 | 3.1 | A | ↑ |
| GC32 | 3.6 | A | ↑ |
| GC33 | 2.3 | B | ↑ |
| GG33 | 2.2 | B | ↑ |
| CC34 | 15 | A | ↑ |
| GC35 | 0.0046 | B | ↓ |
| GC36 | 0.048 | B | ↓ |
| CA42 | 1.9 | B | ↑ |
| CC62 | 0.56 | A | ↓ |

(note) In the table, "A" represents a determination from the autoradiogram in Northern hybridization, and "B" represents a determination based on the electrophoretic gel image of the amplified product by RT-PCR.

3) Acquisition of Cancer-Associated Gene cDNA

A cDNA fragment of each of these cancer-associated genes was then cloned. First, a cDNA library was prepared by fractionating mRNA from a crude RNA sample derived from a cancer tissue or a normal tissue, which was prepared by the method described in Section 1) with mRNA Purification Kit (manufactured by Pharmacia) on an oligo(dT) column, and plating a phage and a host cell XLI-Blue MRF' at a cell density of about 40,000 plaques per rectangular plate in a 10 cm×14 cm plate using a ZAP-cDNA synthesis kit (manufactured by Stratagene) according to the protocols attached to the kit. Thereafter, phage particles were transferred onto a Hybond N+ membrane, and screening was carried out by means of plaque hybridization using a probe identical to that used in Northern hybridization described in Section 2), whereby finding a Uni-ZAP XR clone containing a desired cDNA gene. This recombinant Uni-ZAP XR clone was converted into a pBluescript phagemide by means of an in vitro excision method. The nucleotide sequence of a DNA fragment incorporated into this recombinant phagemide was determined with a fluorescent DNA sequencer (manufactured by ABI). The nucleotide sequences obtained from connection of the nucleotide sequences of the cDNA fragments contained in the cDNA library by means of walking based on the nucleotide sequence of the DNA fragment incorporated into the- phagemide are shown in SEQ ID NOs: 2 to 10, 13, 14 and 68 in Sequence Listing. Since cDNAs for CA11 and GC35 obtained above have smaller sizes of mRNA than the size deduced from the results of Northern hybridization, it is highly possible that 5'-terminal portion in each of the above cDNAs is deleted. Therefore, in order to obtain nearly a whole length of cDNA, cDNA clones were isolated by again screening using a commercially available human gastric cDNA library (manufactured by Takara Shuzo Co., Ltd.) and a probe which was newly prepared based on proximal 5'-terminal region of the sequence obtained above. By means of the above screening, there were obtained a cDNA clone in which base numbers 1 to 76 of SEQ ID NO: 66 in Sequence Listing were added to 5'-terminal of the nucleotide sequence of SEQ ID NO: 1 in a case of CA11; and a cDNA clone in which base numbers 1 to 2530 of SEQ ID NO: 67 in Sequence Listing were added to 5'-terminal of the nucleotide sequence of SEQ ID NO: 11 in Sequence Listing in a case of GC35.

Each of the nucleotide sequences thus obtained was subjected to a homology search with known gene cDNA nucleotide sequences recorded in Genebank by using BLAST program [Altschul, S. F., *Journal of Molecular Biology*, 215, 403–410, (1990)]. As a result, there have not been reported any sequences corresponding to the cDNA of each of CA11, CA13, GC36, GG33, GC35, GC36 and CA42, so that these genes were determined to be novel genes. Further, as a result of searching an open reading frame for a gene product based on the nucleotide sequence contained in each of the gene cDNAs of CA11, CA13, GC36 and CA42, it was deduced that CA11 cDNA encodes the amino acid sequence as shown in SEQ ID NO: 69 in Sequence Listing, CA13 cDNA encodes the amino acid sequence as shown in SEQ ID NO: 18 in Sequence Listing, GC36 cDNA encodes the amino acid sequence as shown in SEQ ID NO: 70 in Sequence Listing, and CA42 cDNA encodes the amino acid sequence as shown in SEQ ID NO: 19 in Sequence Listing, respectively. On the other hand, CC24 corresponded to cytochrome c oxidase subunit I gene, AG26 to p190-B gene, GC31 to cytochrome c oxidase subunit II gene, GC32 to cytochrome b gene, GC33 to integrin α 6 subunit gene, GG24 to F1-ATPase β subunit gene, and CC62 to lactoferrin gene. Moreover, the nucleotide sequence region as shown in SEQ ID NO: 10 in Sequence Listing for the CC34 cDNA was found to be different from a partial region of the cDNA encoding a mitochondrial 16SrRNA by 7 bases.

Incidentally, in the screening of the cDNA library using as a probe an amplified DNA fragment derived from CC34, in addition to the cDNA clone having the nucleotide sequence as shown in SEQ ID NO: 10 in Sequence Listing, an additional, different kind of positive CDNA clone was obtained. There was clarified that the nucleotide sequence of this cDNA had a nucleotide sequence in which T at base number 935 in the nucleotide as shown in SEQ ID NO: 10 in Sequence Listing was substituted with A, and 6 bases consisting of GTTAAG at the 3'-terminal were deleted, of which 1540 bases out of the entire 1546 bases of the entire nucleotide sequence had an identical sequence to a partial region of the cDNA encoding a mitochondrial 16SrRNA.

Example 2

Confirmation of Change in Gene Expression in Cancer Tissue

With respect to each cancer-associated gene confirmed in Example 1, the association of the expression of this gene with the canceration of cells was evaluated by using a cancer tissue different from that used in Example 1.

1) Confirmation of Change in Gene Expression in Cancer Tissue of Patient With Signet Ring Cell Gastric Cancer Using a crude RNA sample prepared in the same manner as in Section 1) of Example 1 from each of a cancer tissue and a control normal tissue excised from a patient with a signet ring cell gastric cancer who was different from the one provided the tissues used in Sections 1) and 2) of Example 1, the expression levels in the cancer tissue and the normal tissue were compared with respect to each of the 14 kinds of cancer-associated genes clarified in Section 3) of Example 1 by using the expression level of the mRNA as an index by means of carrying out Northern hybridization or RT-PCR described in Section 2) of Example 1. As one example, the results of the detection of mRNA for CA11 gene by RT-PCR method are shown in FIG. 3. Specifically, FIG. 3 is a photograph of a fluorescent image of the electrophoresis of a DNA fragment obtained when a change in an expression level of a cancer-associated gene is detected by RT-PCR method. The reaction conditions of the RT-PCR were according to the method described in Section 2) of Example 1, with setting two patterns in the number of the cycles of the PCR, i.e., 25 and 30. In FIG. 3, (a) shows the results of the detection of the expression of a cancer-associated gene CA11, and (b) shows the results of the confirmation of the expression of β-actin as a positive control. In FIG. 3, 2T is an amplified DNA fragment obtained by using as a template a crude RNA sample extracted from a gastric cancer tissue of the patient with a signet ring cell gastric cancer, and 2N is an amplified DNA fragment obtained by using as a template a crude RNA sample extracted from a normal gastric tissue of the patient with the signet ring cell gastric cancer. Also, the numerals "25"and "30"in FIG. 3 are the numbers of the cycles of the nucleic acid amplification in the RT-PCR method. Table 5 shows the results of calculated IODs of the bands on the fluorescent image shown in FIG. 3. Incidentally, each index shown in Table 5 was calculated from Equation 2 described in Section 2) of Example 1.

TABLE 5

| Number of Cycles | 25 | | 30 | |
|---|---|---|---|---|
| Sample Name | 2T | 2N | 2T | 2N |
| CA11 | 365 | 31118 | 6345 | 61742 |
| β-Actin | 710 | 562 | 25115 | 20425 |
| Index Value | 0.0093 | | 0.083 | |

In Table 5, since the IOD values of the band derived from β-actin obtained on the fluorescent image of 2T and 2N were of the similar level in the PCR cycles of 25 and 30, there was clarified that RNAs could be similarly extracted from all samples. However, since the index was less than 1 for both the 25 and 30 cycles of the PCR, there was clarified that CA11 was a gene of which expression level was reduced owing to canceration even also with patients with a signet ring cell gastric cancer. With respect to 13 kinds of cancer-associated genes other than CA11, there was found to be a change in the expression level in the same manner as in Section 2) of Example 1, so that there was clarified that the change in the expression level of each of the 14 kinds of genes as clarified in Section 3) of Example 1 was not a change peculiar to the tissue of the patient tested in Section 1) of Example 1.

Example 3

Construction of Kit for Detecting Cancer

A kit for detecting a cancer utilizing RT-PCR method comprising the following components was constructed.

Specifically, a kit comprises DNaseI, AMV reverse transcriptase, RNase inhibitor, 10×RT-PCR buffer (100 mM Tris-HCl, pH 8.3, 500 mM KCl), 25 mM $MgCl_2$, and a mixture of 2.5 mM each of dATP, dGTP, dCTP and dTTP, an oligo(dT) primer, Taq DNA polymerase, a primer pair specific to each of the genes and a primer pair for amplifying β-actin gene as a positive control shown in Table 2. In the column of the primer pair in Table 2, a symbol of a combination of an alphabet and a numeral indicates the name of a primer, and a number within a parenthesis following each symbol indicates SEQ ID NO: showing the nucleotide sequence of the primer in Sequence Listing.

According to the present invention, it is made possible to simply and rapidly detect cancer. In addition, the presence of a novel nucleic acid associated with the cancer is elucidated.

EQUIVALENT

Those skilled in the art will recognize, or be able to ascertain using simple routine experimentation, many equivalents to the specific embodiments of the invention described in the present specification. Such equivalents are intended to be encompassed in the scope of the following claims.

---

What is claimed is:

1. An isolated nucleic acid encoding a polypeptide consisting of a polypeptide sequence selected from the group consisting of SEQ ID NOS: 17 and 69, wherein the expression level of said isolated nucleic acid is lower in gastric cancer cells compared to normal gastric cells.

2. The isolated nucleic acid according to claim 1, wherein the isolated nucleic acid has the nucleotide sequence selected from the group consisting of SEQ ID NOS: 1 and 66.

3. A kit for detecting a gastric cancer cell, wherein the kit comprises a probe having a nucleotide sequence which is fully complementary to a full length mRNA for a cancer-associated gene to be detected of which a decrease in an expression level as compared to normal gastric cells is to be determined, wherein said cancer-associated gene consists of the nucleotide sequence selected from the group consisting of SEQ ID NOS: 1 and 66.

4. A kit for detecting a gastric cancer cell, comprising:
a probe having a nucleotide sequence which is fully complementary to a full length mRNA for a cancer-associated gene, or a completely complementary strand thereof, wherein said cancer-associated gene comprises the nucleotide sequence selected from the group consisting of SEQ ID NOS: 1 and 66.

* * * * *

SEQUENCE LISTING

<160> NUMBER OF SEQ ID NOS: 70

<210> SEQ ID NO 1
<211> LENGTH: 738
<212> TYPE: DNA
<213> ORGANISM: Homo sapiens
<220> FEATURE:
<223> OTHER INFORMATION: any n or Xaa = unknown

<400> SEQUENCE: 1

```
cctctgtcca ctgctttcgt gaagacaaga tgaagttcac aattgtcttt gctggacttc     60
ttggagtctt tctagctcct gcccttgcta actataatat caacgtcaat gatgacaaca    120
acaatgctgg aagtgggcag cagtcagtga gtgtcaacaa tgaacacaat gtggccaatg    180
ttgacaataa caacggatgg gactcctgga attccatctg ggattatgga aatggctttg    240
ctgcaaccag actctttcaa aagaagacat gcattgtgca caaatgaac aaggaagtca     300 tgccctccat tcaatccctt gatgcactgg tcaaggaaaa gaagcttcag ggtaagggac    360
caggaggacc acctcccaag ggcctgatgt actcagtcaa cccaaacaaa gtcgatgacc    420
tgagcaagtt cggaaaaaac attgcaaaca tgtgtcgtgg gattccaaca tacatggctg    480
aggagatgca agaggcaagc ctgttttttt actcaggaac gtgctacacg accagtgtac    540
tatggattgt ggacatttcc ttctgtggag acacggtgga gaactaaaca attttttaaa    600
gccactatgg atttagtcgt ctgaatatgc tgtgcagaaa aaatatgggc tccagtggtt    660
tttaccatgt cattctgaaa tttttctcta ctagttatgt ttgatttctt taagtttcaa    720
taaaatcatt tagcattg                                                  738
```

<210> SEQ ID NO 2
<211> LENGTH: 2042
<212> TYPE: DNA
<213> ORGANISM: Homo sapiens
<220> FEATURE:

<223> OTHER INFORMATION: any n or Xaa = unknown

<400> SEQUENCE: 2

| | | | | | |
|---|---|---|---|---|---|
| ccgtgacaac | actcctgtca | tattggagtc | caaaacttga | attctgggtt | gaatttttta | 60 |
| aaaatcaggt | accacttgat | ttcatatggg | aaattgaagc | aggaaatatt | gagggcttct | 120 |
| tgatcacaga | aaactcagaa | gagatagtaa | tgctcaggac | aggagcggca | gccccagaac | 180 |
| aggccactca | tttagaattc | tagtgtttca | aaacactttt | gtgtgttgta | tggtcaataa | 240 |
| cattttcat | tactgatggt | gtcattcacc | cattaggtaa | acattccctt | ttaaatgttt | 300 |
| gtttgttttt | tgagacagga | tctcactctg | ttgccagggc | tgtagtgcag | tggtgtgatc | 360 |
| atagctcact | gcaacctcca | cctcccaggc | tcaagcctcc | cgaatagctg | ggactacagg | 420 |
| cgcacaccac | catccccggc | taattttgt | attttttgta | gagacggggt | tttgccatgt | 480 |
| tgccaaggct | ggtttcaaac | tcctggactc | aagaaatcca | cccacctcag | cctcccaaag | 540 |
| tgctaggatt | acaggcatga | gccactgcgc | ccagcctta | taattttg | tatagacatt | 600 |
| cctttggttg | gaagaatatt | tataggcaat | acagtcaaag | tttcaaaata | gcatcacaca | 660 |
| aaacatgttt | ataaatgaac | aggatgtaat | gtacatagat | gacattaaga | aaatttgtat | 720 |
| gaaataattt | agtcatcatg | aaatatttag | ttgtcatata | aaaacccact | gtttgagaat | 780 |
| gatgctactc | tgatctaatg | aatgtgaacg | tgtagatgtt | ttgtgtgtat | tttttaaat | 840 |
| gaaaactcaa | aataagacaa | gtaatttgtt | gataaatatt | tttaaagata | actcagcatg | 900 |
| tttgtaaagc | aggatacatt | ttactaaaag | gttcattggt | tccaatcaca | gctcataggt | 960 |
| agagcaaaga | aagggtggat | ggattgaaaa | gattagcntn | tgtntcggtg | gcaggttccc | 1020 |
| acntcgcaag | caattggaaa | caaaantttn | ggggagtttt | attttgcatt | ngggtgtgtt | 1080 |
| ttatgttaag | caaaacatan | tttagaanca | aatgaaaaag | gcaattgaaa | atcccagnta | 1140 |
| tttcacctag | atggnatagc | caccntgagc | agaacttngt | gatgnttcat | tctgnggaat | 1200 |
| tttgtgcttn | ctactgtata | gtgcatgtgg | tgtaggttac | tctaactggt | tttgtngacg | 1260 |
| taaacattta | aagtgttata | tttttttataa | aaatgtttat | ttttaatgat | atgagaaaaa | 1320 |
| ttttgttagg | ccacaaaaac | actgcactgt | gaacatttta | gaaaaggtat | gtcagactgg | 1380 |
| gattaatgac | agcatgattt | tcaatgactg | taaattgcga | taaggaaatg | tactgattgc | 1440 |
| caatacaccc | caccctcatt | acatcatcag | gacttgaagc | caagggttaa | cccagcaagc | 1500 |
| tacaaagagg | gtgtgtcaca | ctgaaactca | atagttgagt | ttggctgttg | ttgcaggaaa | 1560 |
| atgattataa | ctaaaagctc | tctgatagtg | cagagactta | ccagaagaca | caaggaattg | 1620 |
| tactgaaagag | ctattacaat | ccaaatattg | ccgtttcata | aatgtaataa | gtaatactaa | 1680 |
| ttcacagagt | attgtaaatg | gtggatgaca | aaagaaaatc | tgctctgtgg | aaagaaagaa | 1740 |
| ctgtctctac | cagggtcaag | agcatgaacg | catcaataga | aagractcgg | ggaaacatcc | 1800 |
| catcaacagg | actacacact | tgtatataca | ttcttgagaa | cactgcaatg | tgaaaatcac | 1860 |
| gtttgctatt | tataaacttg | tccttagatt | aatgtgtctg | acagattgt | gggagtaagt | 1920 |
| gattcttcta | agaattagat | acttgtcact | gcctatacct | gcagctgaac | tgaatggtac | 1980 |
| ttcgkatgtt | aatagttgtt | ctgataaatc | atgcaattaa | aataaagtga | tgcaacatct | 2040 |
| tg | | | | | | 2042 |

<210> SEQ ID NO 3
<211> LENGTH: 1539
<212> TYPE: DNA
<213> ORGANISM: Homo sapiens
<220> FEATURE:
<223> OTHER INFORMATION: any n or Xaa = unknown

<400> SEQUENCE: 3

| | | | | | | |
|---|---|---|---|---|---|---|
| atgttcgccg | accgttgact | attctctaca | aaccacaaag | acattggaac | actataccta | 60 |
| ttattcggcg | catgagctgg | agtcctaggc | acagctctaa | gcctccttat | tcgagccgag | 120 |
| ctgggccagc | caggcaacct | tctaggtaac | gaccacatct | acaacgttat | cgtcacagcc | 180 |
| catgcatttg | taataatctt | cttcatagta | atacccatca | taatcggagg | ctttggcaac | 240 |
| tgactagttc | ccctaataat | cggtgccccc | gatatggcgt | tcccccgcat | aaacaacata | 300 |
| agcttctgac | tcttacctcc | ctctctccta | ctcctgctcg | catctgctat | agtagaggcc | 360 |
| ggagcaggaa | caggttgaac | agtctaccct | cccttagcag | ggaactactc | ccaccctgga | 420 |
| gcctccgtag | acctaaccat | cttctcctta | cacctagcag | gtgtctcctc | tatcttaggg | 480 |
| gccatcaatt | tcatcacaac | aattatcaat | ataaaacccc | ctgccataac | ccaataccaa | 540 |
| acgcccctct | cgtctgatc | cgtcctaatc | acagcagtcc | tacttctcct | atctctccca | 600 |
| gtcctagctg | ctggcatcac | tatactacta | acagaccgca | acctcaacac | caccttcttc | 660 |
| gaccccgccg | gaggaggaga | ccccattcta | taccaacacc | tatcctgatt | tttcggtcac | 720 |
| cctgaagttt | atattcttat | cctaccaggc | ttcggaataa | tctcccatat | tgtaacttac | 780 |
| tactccggaa | aaaagaacc | atttggatac | ataggtatgg | tctgagctat | gatatcaatt | 840 |
| ggcttcctag | ggtttatcgt | gtgagcacac | catatattta | cagtaggaat | agacgtagac | 900 |
| acacgagcat | atttcacctc | cgctaccata | atcatcgcta | tccccaccgg | cgtcaaagta | 960 |
| tttagctgac | tcgccacact | ccacggaagc | aatatgaaat | gatctgctgc | agtgctctga | 1020 |
| gccctaggat | tcatctttct | tttcaccgta | ggtggcctga | ctggcattgt | attagcaaac | 1080 |
| tcatcactag | acatcgtact | acacgacacg | tactacgttg | tagctcactt | ccactatgtc | 1140 |
| ctatcaatag | gagctgtatt | tgccatcata | ggaggcttca | ttcactgatt | tcccctattc | 1200 |
| tcaggctaca | ccctagacca | aacctacgcc | aaaatccatt | tcgctatcat | attcatcggc | 1260 |
| gtaaatctaa | ctttcttccc | acaacacttt | ctcggcctat | ccggaatgcc | ccgacgttac | 1320 |
| tcggactacc | ccgatgcata | caccacatga | aatatcctat | catctgtagg | ctcattcatt | 1380 |
| tctctaacag | cagtaatatt | aataattttc | atgatttgag | aagccttcgc | ttcgaagcga | 1440 |
| aaagtcctaa | tagtagaaga | accctccata | aacctggagt | gactatatgg | atgccccca | 1500 |
| ccctaccaca | cattcgaaga | acccgtatac | ataaaatct | | | 1539 |

<210> SEQ ID NO 4
<211> LENGTH: 1807
<212> TYPE: DNA
<213> ORGANISM: Homo sapiens
<220> FEATURE:
<223> OTHER INFORMATION: any n or Xaa = unknown

<400> SEQUENCE: 4

| | | | | | | |
|---|---|---|---|---|---|---|
| gaattctttc | ttcagcccat | gtaaacatga | aataagggt | taaaatgac | ttcattatgg | 60 |
| ggaaaaggga | caggatgcaa | attgttcaaa | ttccgggtgg | ccgctgctcc | ggcctccggg | 120 |
| gccttgcgga | gactcacccc | ttcagcgtcg | ctgccccag | ctcagctctt | actgcgggcc | 180 |
| gtccgacggc | ggtcccatcc | tgtcagggac | tatgcggcgc | aaacatctcc | ttcgccaaaa | 240 |
| gcaggcgccg | ccaccgggcg | catcgtggcg | gtcattggcg | cagtggtgga | cgtccagttt | 300 |
| gatgagggac | taccaccaat | tctaaatgcc | ctggaagtgc | aaggcaggga | gaccagactg | 360 |

-continued

| | |
|---|---|
| gttttggagg tggcccagca tttgggtgag agcacagtaa ggactattgc tatggatggt | 420 |
| acagaaggct tggttagagg ccagaaagta ctggattctg gtgcaccaat caaaattcct | 480 |
| gttggtcctg agactttggg cagaatcatg aatgtcattg gagaacctat tgatgaaaga | 540 |
| ggtcccatca aaccaaaca atttgctccc attcatgctg aggctccaga gttcatggaa | 600 |
| atgagtgttg agcaggaaat tctggtgact ggtatcaagg ttgtcgatct gctagctccc | 660 |
| tatgccaagg gtggcaaaat tgggcttttt ggtggtgctg gagttggcaa gactgtactg | 720 |
| atcatggagt taatcaacaa tgtcgccaaa gcccatggtg gttactctgt gtttgctggt | 780 |
| gttggtgaga ggacccgtga aggcaatgat ttataccatg aaatgattga atctggtgtt | 840 |
| atcaacttaa aagatgccac ctctaaggta gcgctggtat atggtcaaat gaatcaacca | 900 |
| cctggtgctc gtgcccgggt agctctgact gggctgactg tggctgaata cttcagagac | 960 |
| caagaaggtc aagatgtact gctatttatt gataacatct ttcgcttcac ccaggctggt | 1020 |
| tcagaggtgt ctgcattatt gggccgaatc ccttctgctg tgggctatca gcctaccctg | 1080 |
| gccactgaca tgggcactat gcaggaaaga attaccacta ccaagaaggg atctatcacc | 1140 |
| tctgtacagg ctatctatgt gcctgctgat gacttgactg accctgcccc tgctactacg | 1200 |
| tttgcccatt tggatgctac cactgtactg tcgcgtgcca ttgctgagct gggcatctat | 1260 |
| ccagctgtgg atcctctaga ctccacctct cgtatcatga tcccaacat tgttggcagt | 1320 |
| gagcattacg atgttgcccg tgggtgcaa aagatcctgc aggactacaa atccctccag | 1380 |
| gatatcattg ccatcctggg tatggatgaa ctttctgagg aagacaagtt gaccgtgtcc | 1440 |
| cgtgcacgga aaatacagcg tttcttgtct cagccattcc aggttgctga ggtcttcaca | 1500 |
| ggtcatatgg ggaagctggt acccctgaag gagaccatca aaggattcca gcagattttg | 1560 |
| gcaggtgaat atgaccatct cccagaacag gccttctata tggtgggacc cattgaagaa | 1620 |
| gctgtggcaa aagctgataa gctggctgaa gagcattcat cgtgagggt ctttgtcctc | 1680 |
| tgtacttgtc tctctccttg cccctaaccc aaaaagcttc atttttctat ataggctgca | 1740 |
| caagagcctt gattgaagat atattctttc tgaacagtat ttaaggtttc caataaaatc | 1800 |
| ggaattc | 1807 |

<210> SEQ ID NO 5
<211> LENGTH: 4992
<212> TYPE: DNA
<213> ORGANISM: Homo sapiens
<220> FEATURE:
<223> OTHER INFORMATION: any n or Xaa = unknown

<400> SEQUENCE: 5

| | |
|---|---|
| ccgcggtgag ccgcgaggaa gagaggcgag cgagagtgga ggaggaggcg gcggctgcgg | 60 |
| gacggtcccc aggaatgtcg ctgcccccc ccccctgcc gttgaggagg agacggagga | 120 |
| gaccgacgtt gttagggaag atgatcccta tgatctgccg ctgtttctgc acagaaatga | 180 |
| gggaaataca agaaccaaa tacagttcta aatttgggat ctgtattttg agatgatttt | 240 |
| attttcagaa tgagaagcat atctggttac ctttatgaat gtagagacat gagaagagag | 300 |
| ttatgatggc aaaaaacaaa gagcctcgtc ccccatccta taccatcagt atagttggac | 360 |
| tctctgggac tgaaaaagac aaaggtaact gtggagttgg aaagtcttgt ttgtgcaata | 420 |
| gatttgtacg ctcaaaagca gatgaatatt atccagagca tacttctgtg cttagcacca | 480 |
| ttgactttgg aggacgagta gtaaacaatg atcacttttt gtactgggt gacataatac | 540 |
| aaaatagtga agatggagta gaatgcaaaa ttcatgtcat tgaacaaaca gagttcattg | 600 |

```
atgaccagac tttcttgcct catcggagta cgaatttgca accatatata aaacgtgcag    660
ctgcatctaa attgcagtca gcagaaaaac taatgtacat ttgcactgat cagctaggct    720
tagaacaaga ctttgaacag aagcaaatgc ctgaagggaa gctcaacgta gatggatttt    780
tattatgcat tgatgtaagt caaggatgca ataggaagtt tgatgatcaa cttaaatttg    840
tgaataacct ttttgtccag ttatcaaaat caaaaaaacc tgtaataata gcagcaacta    900
aatgtgatga atgcgtgggt cattatctta gagaagttca ggcatttgct tcaaataaaa    960
agaaccttct tgtagtggaa acactcagcg caataaaagt caacattgaa acatgtttta   1020
ctgcactggt acaaatgttg gataaaactc gtagcaagcc taaaattatt ccctatttgg   1080
atgcttataa aacacagaga caacttgttg tcacagcaac agataagttt gaaaaacttg   1140
tgcagactgt gagagattat catgcaactt ggaaaactgt tagtaataaa ttaaaaaatc   1200
atcctgatta tgaagaatac atcaacttag agggaacaag aaaggccaga atacattct    1260 caaacatat agaacaactt aaacaggaac atataagaaa aaggagagaa gagtatataa   1320
atactttacc aagagctttt aacactcttt tgccaaatct agaagagatt gaacatttga   1380
attggtcaga agctttgaag ttaatggaaa agagagcaga tttccagtta tgttttgtgg   1440
tgctagaaaa aactccttgg gatgaaactg accatataga caaaattaat gataggcgga   1500
ttccatttga cctcctgagc actttagaag ctgaaaaagt ctatcagaac catgtacagc   1560
atctgatatc cgagaagagg agggtggaaa tgaaggaaaa attcaaaaag actttggaaa   1620
aaattcaatt catttcacca ggcagccat gggaggaagt tatgtgcttt gttatggagg   1680
atgaagccta caaatatatc actgaggctg atagcaaaga ggtatatggt aggcatcagc   1740
gagaaatagt tgaaaaagcc aaagaagagt ttcaagaaat gcttttttgag cattctgaac   1800 ttttttatga tttagatctt aatgcaacac ctagttcaga taaatgagt gaaattcata   1860 cagttctgag tgaagaacct agatataaag ctttacagaa acttgcacct gatagggaat   1920
cccttctact taagcatata ggatttgttt atcatcccac taaagaaaca tgtcttagtg   1980
gccaaaattg tacagacatt aaagtggagc agttacttgc tagtagtctt ttacagttgg   2040
atcatggccg cttaagatta tatcacgata gtaccaatat agataaagtt aacctttta   2100 ttttagggaa ggatggcctt gcccaagaac tagcaaatga gataaggaca caatccactg   2160
atgatgagta tgccttagat ggaaaaattt atgaacttga tcttcggccg gttgatgcca   2220
aatcgcctta cttttttgagt cagttatgga ctgccgcctt taaaccacat gggtgcttct   2280
gtgtatttaa ttccattgag tcattgagtt ttattgggga attttattgg gaaaataagaa   2340 ctgaagcttc tcagatcaga aaagataaat acatggctaa tcttccattt acattaattc   2400
tggctaatca gagagattcc attagtaaga atctaccaat tctcaggcac caagggcagc   2460
agttggcaaa caagttgcaa tgtccttttg tagatgtacc tgctggtaca tatcctcgta   2520
aatttaatga aacccaaata aagcaagctc tcagaggagt attggaatca gttaaacaca   2580
atttggatgt ggtgagccca attcctgcca ataaggactt atcagaagct gacttgagaa   2640
ttgtcatgtg cgccatgtgt ggagatccat ttagtgtgga tcttattctt tcacccttcc   2700
ttgattctca ttccttgcagt gctgctcaag ctggacagaa taattcccta atgcttgata   2760
aaatcattgg tgaaaaaagg aggcgaatac agatcacaat attatcatac cactcttcaa   2820
ttggagtaag aaaagatgaa ctagttcatg ggtatatatt agtttactct gcaaaacgga   2880
aagcttcgat gggaatgctt cgagcatttc tatcagaagt tcaagacacc attcctgtac   2940
```

-continued

| | |
|---|---|
| agctggtggc agttactgac agccaagcag atttttttga aaatgaggct atcaaagagt | 3000 |
| taatgactga aggagaacac attgcaactg agatcactgc taaatttaca gcactgtatt | 3060 |
| ctttatctca gtatcatcgg caaactgagg tctttactct gttttttagt gatgttctag | 3120 |
| agaaaaaaaa tatgatagaa aattcttatt tgtctgataa tacaagggaa tcaacccatc | 3180 |
| aaagtgaaga tgttttttcta ccatctccca gagactgttt tccctataat aactaccctg | 3240 |
| attcagatga tgacacagaa gcaccacctc cttatagtcc aattggggat gatgtacagt | 3300 |
| tgcttccaac acctagtgac cgttccagat atagattaga tttggaagga aatgagtatc | 3360 |
| ctattcatag taccccaaac tgtcatgacc atgaacgcaa ccataaagtg cctccaccta | 3420 |
| ttaaacctaa accagttgta cctaagacaa atgtgaaagc gctcgttcca aacctttttaa | 3480 |
| gggcaattga agctggtatt ggtaaaaatc caagaaagca gacttcccgg gtgcctttcg | 3540 |
| gtcctgaaga tatggatcct tcagataact atgcggaacc cattgataca attttcaaac | 3600 |
| agaagggcta ttctgatgag atttatgttg tcccagatga tagtcaaaat cgtattaaaa | 3660 |
| ttcgaaactc atttgtaaat aacacccaag gagatgaaga aaatgggttt tctgatagac | 3720 |
| ctcaaaaagt catggggaac ggaggccttc aaaatacaaa tataaatcta aaaccttgtt | 3780 |
| tagtaaagcc aagtcatact atagaagaac acattcagat gccagtgatg atgaggcttt | 3840 |
| caccacttct aaaaccaaaa agaaaaggaa gacatcgtgg aagtgaagaa gatccacttc | 3900 |
| tttctcctgt tgaaacttgg aaaggtggta ttgataatcc tgcaatcact tctgaccagg | 3960 |
| agttagatga taagaagatg aagaagaaaa cccacaaagt gaaagaagat aaaaaaaaga | 4020 |
| aaactaagaa cttcaatcca ccaacacgta gaaattggga agtaattac tttgggatgc | 4080 |
| ccctccagga tctggttaca gctgagaagc ccataccact atttgttgag aaatgtgtgg | 4140 |
| aatttattga agatacaggg ttatgtaccg agagactcta ccgtgtcagc gggaataaaa | 4200 |
| ctgaccaaga aaatattcaa aagcagtttg ttcaagatca taatatcaat ctagtgtcaa | 4260 |
| tggaagtaac agtaaatgct gtagctggag cccttaaagc tttctttgca gatctgccag | 4320 |
| atcctttaat tccatattct cttcatccag aactattgga agcagcaaaa atcccggata | 4380 |
| aaacagaacg tcttcatgcc ttgaaagaaa ttgttaagaa atttcatcct gtaaactatg | 4440 |
| atgtattcag atacgtgata acacatctaa acagggttag tcagcaacat aaaatcaacc | 4500 |
| taatgacagc agacaactta tccatctgtt ttggccaacc cttgatgaga cctgatttga | 4560 |
| aatcgatgga gtttctgtct actactaaga ttcatcaatc tgttgttgaa acattcattc | 4620 |
| agcagtgtca gttttttcttt tacaatggag aaattgtaga acgacaaac attgtggctc | 4680 |
| ctccaccacc ttcaaaccca ggacagttgg tggaaccaat ggtgccactt cagttgccgc | 4740 |
| caccattgca acctcagctg atacaaccac aattacaaac ggatcctctt ggtattatat | 4800 |
| gagtaggaag tgattgcaaa caggctggat ttggacaaaa agcaaatcta gacatgcatg | 4860 |
| tttcagggtt cagtagtata cttcatgttt catacagata attcacattc aaaattacat | 4920 |
| tttctctttg aactagatgg tattccttat tcacttacat tacaaatcta agaccatgtg | 4980 |
| ataagcatga ct | 4992 |

<210> SEQ ID NO 6
<211> LENGTH: 708
<212> TYPE: DNA
<213> ORGANISM: Homo sapiens
<220> FEATURE:
<223> OTHER INFORMATION: any n or Xaa = unknown

<400> SEQUENCE: 6

-continued

```
tatggcacat gcagcgcaag taggtctaca agacgctact tcccctatca tagaagagct      60 tatcacctt  catgatcacg ccctcataat cattttcctt atctgcttcc tagtcctgta      120 tgccctttc  ctaacactca caacaaaact aactaatact aacatctcag acgctcagga      180
aatagaaacc gtctgaacta tcctgcccgc catcatccta gtcctcatcg ccctcccatc      240
cctacgcatc ctttacataa cagacgaggt caacgatccc tcccttacca tcaaatcaat      300
tggccaccaa tggtactgaa cctacgagta caccgactac ggcggactaa tcttcaactc      360
ctacatactt cccccattat tcctagaacc aggcgacctg cgactccttg acgttgacaa      420
tcgagtagta ctcccgattg aagcccccat tcgtataata attacatcac aagacgtctt      480
gcactcatga gctgtcccca cattaggctt aaaaacagat gcaattcccg gacgtctaaa      540
ccaaaccact ttcaccgcta cacgaccggg ggtatactac ggtcaatgct ctgaaatctg      600
tggagcaaac cacagtttca tgcccatcgt cctagaatta ttcccctaa  aaatctttga      660 aatagggccc gtatttaccc tatagcaccc cctctacccc ctctagag               708
```

<210> SEQ ID NO 7
<211> LENGTH: 1140
<212> TYPE: DNA
<213> ORGANISM: Homo sapiens
<220> FEATURE:
<223> OTHER INFORMATION: any n or Xaa = unknown

<400> SEQUENCE: 7

```
atgaccccaa tacgcaaaat taaccccta ataaaattaa ttaaccactc attcatcgac      60
ctccccaccc catccaacat ctccgcatga tgaaacttcg gctcactcct tggcgcctgc     120
ctgatcctcc aaatcaccac aggactattc ctagccatgc actactcacc agacgcctca     180 accgccttt  catcaatcgc ccacatcact cgagacgtaa attatggctg aatcatccgc     240
taccttcacg ccaatggcgc ctcaatattc tttatctgcc tcttcctaca catcgggcga     300
ggcctatatt acggatcatt tctctactca gaaacctgaa acatcggcat tatcctcctg     360
cttgcaacta tagcaacagc cttcataggt tatgtcctcc cgtgaggcca aatatcattc     420 tgagggcca  cagtaattac aaacttacta tccgccatcc catacattgg gacagaccta     480
gttcaatgaa tctgaggagg ctactcagta gacagtccca ccctcacacg attctttacc     540
tttcacttca tcttgccctt cattattgca accctagcag cactccacct cctattcttg     600
cacgaaacgg gatcaaacaa cccctagga atcacctccc attccgataa aatcaccttc     660 caccctttact acacaatcaa agacaccctc ggcttacttc tcttccttct ctccttaatg     720
acattaacac tattctcacc agacctccta ggcgacccca caattatac  cctagccaac     780 cccttaaaca cccctcccca catcaagccc gaatgatatt tcctattcgc ctacacaatt     840
ctccgatccg tccctaacaa actaggaggc gtccttgccc tattactatc catcctcatc     900
ctagcaataa tccccatcct ccatatatcc aaacaacaaa gcataatatt tcgcccacta     960
agccaatcac tttattgact cctagccgca gacctcctca ttctaacctg aatcggagga    1020
caaccagtaa gctacccttt taccatcatt ggacaagtag catccgtact atacttcaca    1080
acaatcctaa tcctaatacc aactatctcc ctaattgaaa acaaaatact caaatgggcc    1140
```

<210> SEQ ID NO 8
<211> LENGTH: 5629
<212> TYPE: DNA
<213> ORGANISM: Homo sapiens
<220> FEATURE:

<223> OTHER INFORMATION: any n or Xaa = unknown

<400> SEQUENCE: 8

| | | | | | |
|---|---|---|---|---|---|
| gcgcgaccgt | cccggggtg | gggccgggcg | cagcggcgag | aggaggcgaa | ggtggctgcg | 60 |
| gtagcagcag | cgcggcagcc | tcggacccag | cccggagcgc | agggcggccg | ctgcaggtcc | 120 |
| ccgctcccct | cccgtgcgt | ccgcccatgc | cgccgccgg | gcagctgtgc | ttgctctacc | 180 |
| tgtcggcggg | gctcctgtcc | cggctcggcg | cagccttcaa | cttggacact | cgggaggaca | 240 |
| acgtgatccg | gaaatatgga | gaccccggga | gcctcttcgg | cttctcgctg | gccatgcact | 300 |
| ggcaactgca | gcccgaggac | aagcggctgt | tgctcgtggg | ggccccgcgc | ggagaagcgc | 360 |
| ttccactgca | gagagccaac | agaacgggag | ggctgtacag | ctgcgacatc | accgcccggg | 420 |
| ggccatgcac | gcggatcgag | tttgataacg | atgctgaccc | cacgtcagaa | agcaaggaag | 480 |
| atcagtggat | ggggtcacc | gtccagagcc | aaggtccagg | gggcaaggtc | gtgacatgtg | 540 |
| ctcaccgata | tgaaaaagg | cagcatgtta | atacgaagca | ggaatcccga | gacatctttg | 600 |
| ggcggtgtta | tgtcctgagt | cagaatctca | ggattgaaga | cgatatggat | gggggagatt | 660 |
| ggagcttttg | tgatgggcga | ttgagaggcc | atgagaaatt | tggctcttgc | cagcaaggtg | 720 |
| tagcagctac | ttttactaaa | gactttcatt | acattgtatt | tggagccccg | ggtacttata | 780 |
| actggaaagg | gattgttcgt | gtagagcaaa | agaataacac | ttttttttgac | atgaacatct | 840 |
| ttgaagatgg | gccttatgaa | gttggtggag | agactgagca | tgatgaaagt | ctcgttcctg | 900 |
| ttcctgctaa | cagttactta | ggttttttctt | tggactcagg | gaaaggtatt | gtttctaaag | 960 |
| atgagatcac | ttttgtatct | ggtgctccca | gagccaatca | cagtggagcc | gtggttttgc | 1020 |
| tgaagagaga | catgaagtct | gcacatctcc | tccctgagca | catattcgat | ggagaaggtc | 1080 |
| tggcctcttc | atttggctat | gatgtggcgg | tggtggacct | caacaaggat | gggtggcaag | 1140 |
| atatagttat | tggagcccca | cagtattttg | atagagatgg | agaagttgga | ggtgcagtgt | 1200 |
| atgtctacat | gaaccagcaa | ggcagatgga | ataatgtgaa | gccaattcgt | cttaatggaa | 1260 |
| ccaaagattc | tatgttttggc | attgcagtaa | aaaatattgg | agatattaat | caagatggct | 1320 |
| acccagatat | tgcagttgga | gctccgtatg | atgacttggg | aaaggttttt | atctatcatg | 1380 |
| gatctgcaaa | tggaataaat | accaaaccaa | cacaggttct | caagggtata | tcaccttatt | 1440 |
| ttggatattc | aattgctgga | acatggacc | ttgatcgaaa | ttcctaccct | gatgttgctg | 1500 |
| ttggttccct | ctcagattca | gtaactattt | tcagatcccg | gcctgtgatt | aatattcaga | 1560 |
| aaaccatcac | agtaactcct | aacagaattg | acctccgcca | gaaaacagcg | tgtggggcgc | 1620 |
| ctagtgggat | atgcctccag | gttaaatcct | gttttgaata | tactgctaac | cccgctggtt | 1680 |
| ataatccttc | aatatcaatt | gtgggcacac | ttgaagctga | aaagaaaga | agaaaatctg | 1740 |
| ggctatcctc | aagagttcag | tttcgaaacc | aaggttctga | gcccaaatat | actcaagaac | 1800 |
| taactctgaa | gaggcagaaa | cagaaagtgt | gcatggagga | aaccctgtgg | ctacaggata | 1860 |
| atatcagaga | taaactgcgt | cccattccca | taactgcctc | agtggagatc | caagagccaa | 1920 |
| gctctcgtag | gcgagtgaat | tcacttccag | aagttcttcc | aattctgaat | tcagatgaac | 1980 |
| ccaagacagc | tcatattgat | gttcacttct | taaaagaggg | atgtggagac | gacaatgtat | 2040 |
| gtaacagcaa | ccttaaacta | gaatataaat | tttgcacccg | agaaggaaat | caagacaaat | 2100 |
| tttcttattt | accaattcaa | aaaggtgtac | cagaactagt | tctaaaagat | cagaaggata | 2160 |
| ttgctttaga | aataacagtg | acaaacagcc | cttccaaccc | aaggaatccc | acaaaagatg | 2220 |
| gcgatgacgc | ccatgaggct | aaactgattg | caacgttccc | agacacttta | acctattctg | 2280 |

```
catatagaga actgagggct ttccctgaga aacagttgag ttgtgttgcc aaccagaatg    2340
gctcgcaagc tgactgtgag ctcggaaatc cttttaaaag aaattcaaat gtcacttttt    2400
atttggtttt aagtacaact gaagtcacct ttgacacccc atatctggat attaatctga    2460
agttagaaac aacaagcaat caagataatt tggctccaat tacagctaaa gcaaaagtgg    2520
ttattgaact gcttttatcg gtctcgggag ttgctaaacc ttcccaggtg tattttggag    2580
gtacagttgt tggcgagcaa gctatgaaat ctgaagatga agtgggaagt ttaatagagt    2640
atgaattcag ggtaataaac ttaggtaaac ctcttacaaa cctcggcaca gcaaccttga    2700
acattcagtg gccaaaagaa attagcaatg ggaaatggtt gctttatttg gtgaaagtag    2760
aatccaaagg attggaaaag gtaacttgtg agccacaaaa ggagataaac tccctgaacc    2820
taacggagtc tcacaactca agaaagaaac gggaaattac tgaaaaacag atagatgata    2880
acagaaaatt ttctttattt gctgaaagaa aataccagac tcttaactgt agcgtgaacg    2940
tgaactgtgt gaacatcaga tgcccgctgc gggggctgga cagcaaggcg tctcttattt    3000
tgcgctcgag gttatggaac agcacatttc tagaggaata ttccaaactg aactacttgg    3060
acattctcat gcgagccttc attgatgtga ctgctgctgc cgaaaatatc aggctgccaa    3120
atgcaggcac tcaggttcga gtgactgtgt ttccctcaaa gactgtagct cagtattcgg    3180
gagtaccttg gtggatcatc ctagtggcta ttctcgctgg gatcttgatg cttgctttat    3240
tagtgtttat actatggaag tgtggtttct caagagaaa taagaaagat cattatgatg    3300
ccacatatca caaggctgag atccatgctc agccatctga taaagagagg cttacttctg    3360
atgcatagta ttgatctact tctgtaattg tgtggattct ttaaacgctc taggtacgat    3420
gacagtgttc cccgatacca tgctgtaagg atccggaaag aagagcgaga gatcaaagat    3480
gaaaagtata ttgataacct tgaaaaaaaa cagtggatca caaagtggaa cagaaatgaa    3540
agctactcat agcgggggcc taaaaaaaaa aaagcttcac agtacccaaa ctgcttttc    3600 caactcagaa attcaatttg gatttaaaag cctgctcaat ccctgaggac tgattccaga    3660
gtgactacac acagtacgaa cctacagttt taactgtgga tattgttacg tagcctaagg    3720
ctcctgtttt gcacagccaa atttaaaact gttggaatgg attttctttt aactgccgta    3780
atttaacttt ctgggttgcc tttgttttg gcgtggctga cttacatcat gtgttgggga    3840
agggcctgcc cagttgcact caggtgcat cctccagata gtgtagctga ggaggcacct    3900
acactcacct gcactaacag agtggccgtc ctaacctcgg gcctgctgcg cagacgtcca    3960
tcacgttagc tgtcccacat cacaagacta tgccattggg gtagttgtgt ttcaacggaa    4020
agtgctgtct taaactaaat gtgcaataga aggtgatgtt gccatcctac cgtcttttcc    4080
tgtttcctag ctgtgtgaat acctgctcac gtcaaatgca tacaagtttc attctcccttt    4140 tcactaaaaa cacacaggtg caacagactt gaatgctagt tatacttatt tgtatatggt    4200
atttattttt tctttctttt acaaaccatt ttgttattga ctaacaggcc aaagagtctc    4260
cagtttaccc ttcaggttgg tttaatcaat cagaattaga attagagcat gggagggtca    4320
tcactatgac ctaaattatt tactgcaaaa agaaaatctt tataaatgta ccagagagag    4380 ttgtttaat aacttatcta taaactataa cctctccttc atgacagcct ccaccccaca    4440
acccaaaagg tttaagaaat agaattataa ctgtaaagat gtttatttca ggcattggat    4500
attttttact ttagaagcct gcataatgtt tctggattta catactgtaa cattcaggaa    4560
ttcttggaga agatgggttt attcactgaa ctctagtgcg gtttactcac tgctgcaaat    4620
```

-continued

```
actgtatatt caggacttga aagaaatggt gaatgcctat ggaactagtg gatccaaact    4680
gatccagtat aagactactg aatctgctac caaaacagtt aatcagtgag tcgagtgttc    4740 tatttttgt tttgtttcct cccctatctg tattcccaaa aattactttg gggctaattt    4800
aacaagaact ttaaattgtg ttttaattgt aaaaatggca gggggtggaa ttattactct    4860
atacattcaa cagagactga atagatatga aagctgattt tttttaatta ccatgcttca    4920
caatgttaag ttatatgggg agcaacagca aacaggtgct aatttgtttt ggatatagta    4980
taagcagtgt ctgtgttttg aaagaataga acacagtttg tagtgccact gttgttttgg    5040
gggggctttt ttttcttttt ccggaaaatc cttaaacctt aagatactaa ggacgttgtt    5100
ttggttgtac ttggaattct tagtcacaaa atatattttg tttacaaaaa tttctgtaaa    5160
acaggttata acagtgttta aagtctcagt ttcttgcttg gggaacttgt gtccctaatg    5220
tgttagattg ctagattgct aaggagctga tacttgacag ttttttagac ctgtgttact    5280 aaaaaaaga tgaatgtcgg aaaagggtgt tgggagggtg gtcaacaaag aaacaaagat    5340
gttatggtgt ttagacttat ggttgttaaa aatgtcatct caagtcaagt cactggtctg    5400
tttgcatttg atacattttt gtactaacta gcattgtaaa attatttcat gattagaaat    5460
tacctgtgga tatttgtata aaagtgtgaa ataaattttt tataaaagtg ttcattgttt    5520
cgtaacacag cattgtatat gtgaagcaaa ctctaaaatt ataaatgaca acctgaatta    5580
tctatttcat caaaaaaaaa aaaaaaaaa actttatggg cacaactgg               5629
```

<210> SEQ ID NO 9
<211> LENGTH: 580
<212> TYPE: DNA
<213> ORGANISM: Homo sapiens
<220> FEATURE:
<223> OTHER INFORMATION: any n or Xaa = unknown

<400> SEQUENCE: 9

```
ccatccaatg aggccacctc tttctaaact cagactcttc atttagggag gtgagttcca     60
ttaaggaact tgagattttc agataaatgg aaaatactag ataaagaggt atctcataga    120
tagcaaaggt aaactctcat acaatcattg agctaggaca ttaatggttc agtggttccc    180
aattctagat atacattaaa ataaattgaa aagccttttta aaaatacatg attactggac    240
ctactgaatt atatcctttg gggagcccaa gaacttatta aattctctgg gctatttta    300 tgatttctct gagctgttac tgggaactac tgattgaatc catytttat agtaatgttt    360 ccaacagaag gctgtttscc tttgcttaac attatttcca gtgaagtatt attttccatt    420
ctggagacag ttcaaaagtt tttttaagta acagctttat tgagacaatt tatatsccgt    480
acaattcacc taaagtgtgt aattcagttg tttttagtat gttcacagaa ttgtgcagct    540
tgcatctatc accacaaatt tagaaccttg tcataatccc                          580
```

<210> SEQ ID NO 10
<211> LENGTH: 1552
<212> TYPE: DNA
<213> ORGANISM: Homo sapiens
<220> FEATURE:
<223> OTHER INFORMATION: any n or Xaa = unknown

<400> SEQUENCE: 10

```
cccaaaccca ctccacctta ctaccagaca accttagcca aaccatttac ccaaataaag     60
tataggcgat agaaattgaa acctggcgca atagatatag taccgcaagg gaaagatgaa    120
aaattataac caagcataat atagcaagga ctaaccccta taccttctgc ataatgaatt    180
```

-continued

```
aactagaaat aactttgcaa ggagagccaa agctaagacc cccgaaacca gacgagctac      240
ctaagaacag ctaaaagagc acaccgtct atgtagcaaa atagtgggaa gatttatagg       300
tagaggcgac aaacctaccg agcctggtga tagctggttg tccaagatag aatcttagtt     360
caactttaaa tttgcccaca gaaccctcta atccccttg taaatttaac tgttagtcca      420
aagaggaaca gctctttgga cactaggaaa aaaccttgta gagagagtaa aaatttaac      480 acccatagta ggcctaaaag cagccaccaa ttaagaaagc gttcaagctc aacacccact     540
acctaaaaaa tcccaaacat ataactgaac tcctcacacc caattggacc aatctatcac     600
cctatagaag aactaatgtt agtataagta acatgaaaac attctcctcc gcataagcct    660
gcgtcagatt aaaacactga actgacaatt aacagcccaa tatctacaat caaccaacaa     720
gtcattatta ccctcactgt caacccaaca caggcatgct cataaggaaa ggttaaaaaa    780
agtaaaagga actcggcaaa tcttacccccg cctgtttacc aaaacatca cctctagcat    840 caccagtatt agaggcaccg cctgcccagt gacacatgtt taacggccgc ggtaccctaa    900
ccgtgcaaag gtagcataat cacttgttcc ttaattaggg acccgtatga atggctccac    960
gagggttcag ctgtctctta cttttaacca gtgaaattga cctgcccgtg aagaggcggg  1020
catgacacag caagacgaga agaccctatg gagctttaat ttattaatgc aaacagtacc  1080
taacaaacct acaggtccta aactaccaaa cctgcattaa aaatttcggt tggggcgacc  1140
tcggagcaga acccaacctc cgagcagtac atgctaagac ttcaccagtc aaagcgaact  1200
actatactca attgatccaa taacttgacc aacggaacaa gttaccctag ggataacagc  1260
gcaatcctat tctagagtcc atatcaacaa tagggtttac gacctcgatg ttggatcagg  1320
acatcccgat ggtgcagccg ctattaaagg ttcgtttgtt caacgattaa agtcctacgt  1380
gatctgagtt cagaccggag taatccaggt cggtttctat ctacttcaaa ttcctccctg  1440
tacgaaagga caagagaaat aaggcctact tcacaaagcg ccttcccccg taaatgatat  1500
catctcaact tagtattata cccacaccca cccaagaaca gggtttgtta ag           1552
```

<210> SEQ ID NO 11
<211> LENGTH: 2116
<212> TYPE: DNA
<213> ORGANISM: Homo sapiens
<220> FEATURE:
<223> OTHER INFORMATION: any n or Xaa = unknown

<400> SEQUENCE: 11

```
gggtggcaga atattagtct agctatctcc cattgctctc acgcgccatc tactggattt     60
catcccaaac tacaacacga aaaactgcta attttcctgc ctgccaggcc gaggactgga   120
attcaacaga ctgtttagag cctttgcctc ctgaaaactt ccagaaatga agccaactga   180
ctatattcag tttacaccag agttaaagga acgccaaccc tcccagatga gaaagaatca   240
gtgcaagaac tgtagcaatt taaaaaacca gagcgtcccc ttacctccaa atgagcccac   300
tagctccaca gcaattgttc ttaaccaatc tgaaatgatg agcatggaat tcagaatctg   360
aatggcaatg aagcttatag atatccagga gaaagttgaa atgcaatcca aggaaaccaa   420
gcaatccagt gaaatggttt aagagctgaa agataaaata ncaattttac aaaagaccca   480
aactgagctt attgagttca aaaagaatt tcataataca atcagaagta ttaatagcag   540
aataggccaa gctgaggaaa gaatctcaga gcttgacccc tggttctttg aatcaactta   600
gacaaaaata aagaaaaaag agtttttaaga aatgaacaca atctcccaga aatatgagat   660
```

-continued

```
tatgtwaaga gacaaaatct atgactcatt gccatccctg agagagaagg agagagaata    720
agcaacttgg aaaatatatt tggggacata gcccacaaaa atttccctaa tctctctaga    780
gaggttgaca tgtaaattca agaaatacag aagaccttgg ccagataata tacaagatga    840
ccatccccaa ggcacatagt catcagattc accatggtca atgcaaaaga aaaaaatctt    900
aaagacagct agggagaagg gtcaagtcac atgcagaagg actctcatta ggctggcagt    960
ggacctctca gcagaaacct gacaagccag aagagatgga gggagagggg tctatttttg   1020
tcatccttaa agaaaaaaaa ttccaaccaa gagtctcata cactgccaaa ctaagcttcc   1080
taagtgaagg agaaataaaa accttctcag acaagcaaat gctgaaggaa ttcaactaga   1140
ccagcctaac aagaggtcct aagggagtgc tgaatatgga ctcaaaagaa taacacctgc   1200
taccacaaac actcacttaa gcacacagcc caacgacact ataggcaatt acacagtaag   1260
tctacataac aacacaatga caggatcaac atctcacaca tcaatactaa ccccgagtgt   1320 aaagggcta aatgccccac ttaaaagaca tagagtgtca agcttgataa aaagacaaga   1380
tccaatcatc cactatttc aagagctcta tgttatgtgt aatgacaccc acagactcaa   1440
agacttggag aaagatttat catgcaaaat cagaaaacaa aaaagagcag gagtcactag   1500
ttttatatca gacaaaacag actttaaacc cttaataatt aagaaagaca agaagggta   1560 tttcctggac cacagaaggc ttattggaaa aaaggacata atgacaaagg gtacaatcca   1620
acaagaagtt ttaactattc taaatatata cacaccccaac attggagcac ccagatttat   1680
aaaacaagta cttctcgatc tacaagaaga cttagacagc cacacaataa tagtgggaga   1740
ctttcacatc ctacttacag atcattgaga cagaaaacta ataaaagaac tctggactta   1800
aacttgttac ttgaccaatt ggacctaata gatatccaca gaaaacttca cccaacaaag   1860
acagaatata cattcttctt atctgcacat ggaacacatt ccaagatcaa tcacatgcta   1920
ggtaagaaag caagtctcaa taattaaaa aaaattgaaa tcatacgaac cttaatatca   1980
gaccacaatg taattaaaaa taaatcaata tcaagaagat ctcatacata aatacatgaa   2040
aattaaacaa cttactcctg aataactctt gtgtgaacat caaaattcag gaagaaataa   2100
aaaattattt gaaatt                                                  2116
```

<210> SEQ ID NO 12
<211> LENGTH: 173
<212> TYPE: DNA
<213> ORGANISM: Homo sapiens
<220> FEATURE:
<223> OTHER INFORMATION: any n or Xaa = unknown

<400> SEQUENCE: 12

```
gcgatccaca aatgggaggt gacggtccat cagggaagct gggttcgcgg ctccacggct     60
gggggctgcc gcaatttcct ggatacctt tggaccaatc cacaaataaa attgtctctg    120
actgagaaag atgaggggca ggaggagtgt agtttccttg tagccctgat gca          173
```

<210> SEQ ID NO 13
<211> LENGTH: 655
<212> TYPE: DNA
<213> ORGANISM: Homo sapiens
<220> FEATURE:
<223> OTHER INFORMATION: any n or Xaa = unknown

<400> SEQUENCE: 13

```
ctgatccatg ggccagcagc atcaatatta cctgggagct tacagaaatg cagaatttca     60
ggcccactgc agatctaccg aatcaaaatc ttcctttagc aaaatttctc aaacgattag    120
```
cactggccta catccatttt atccttcctt agctattagg gatgtgaggt ccgagggctt    180
caaaaggtcc ccggaatagc ttgttccttc atccactgtg tcctattcat tcttcagcta    240
actccagcaa tgagctgaaa ctcattcatc accettgctg agttttcttc tcaatcctta    300
ttcctaattc tggttctaga tgagcccatc ctacccagtg ttgtatttt tgtagccagt    360 gtgggacaca ggagattggc agaccaacac agctagcctc tctctagccc tccctccacc    420
tctaagtcac taacaatcca tgtttgttca gtttgttgac atgtggcatg ttcatttgtt    480
cacaacttaa tcacggggga catttcagaa aaatgtgtac taagttaaaa ccatgtttag    540
tctcctacaa cttgtacatt ttcatttct cttatcagta gattgtcctt gttgacatag    600
ctcatgcatg aggacacata gcagtacaca cacattgaat gaattgttag tcatg         655

<210> SEQ ID NO 14
<211> LENGTH: 2619
<212> TYPE: DNA
<213> ORGANISM: Homo sapiens
<220> FEATURE:
<223> OTHER INFORMATION: any n or Xaa = unknown

<400> SEQUENCE: 14
gactcctagg ggcttgcaga cctagtggga gagaaagaac atcgcagcag ccaggcagaa    60
ccaggacagg tgaggtgcag gctggctttc tctcgcagc gcggtgtgga gtcctgtcct    120
gcctcagggc ttttcggagc ctggatcctc aaggaacaag tagacctggc cgcggggagt    180
ggggagggaa ggggtgtcta ttgggcaaca gggcggcaaa gccctgaata aaggggcgca    240
gggcaggcgc aagtgcagag ccttcgtttg ccaagtcgcc tccagaccgc agacatgaaa    300
cttgtcttcc tcgtcctgct gttcctcggg gccctcggac tgtgtctggc tggccgtagg    360
agaaggagtg ttcagtggtg cgccgtatcc aacccgagg ccacaaaatg cttccaatgg    420
caaaggaata tgagaaaagt gcgtggccct cctgtcagct gcataaagag agactccccc    480
atccagtgta tccaggccat tgcggaaaac agggccgatg ctgtgaccct tgatggtggt    540
ttcatatacg aggcaggcct ggccccctac aaactgcgac ctgtagcggc ggaagtctac    600
gggaccgaaa gacagccacg aactcactat tatgccgtgg ctgtggtgaa gaagggcggc    660
agctttcagc tgaacgaact gcaaggtctg aagtcctgcc acacaggcct tcgcaggacc    720
gctggatgga atgtccctac aggacacttc gtccattct tgaattggac gggtccacct    780
gagcccattg aggcagctgt ggccaggttc ttctcagcca gctgtgttcc cggtgcagat    840
aaaggacagt tccccaacct gtgtcgcctg tgtcgggga caggagaaaa caaatgtgcc    900
ttctcctccc aggaaccgta cttcagctac tctggtgcct tcaagtgtct gagagacggg    960
gctggagacg tggcttttat cagagagagc acagtgtttg aggacctgtc agacgaggct    1020
gaaagggacg agtatgagtt actctgccca gacaacactc ggaagccagt ggacaagttc    1080
aaagactgcc atctggcccg ggtcccttct catgccgttg tggcacgaag tgtgaatggc    1140
aaggaggatg ccatctggaa tcttctccgc aggcacagg aaaagtttgg aaaggacaag    1200
tcaccgaaat tccagctctt tggctccct agtgggcaga agatctgct gttcaaggac    1260 tctgccattg ggtttcgag ggtgccccg aggatagatt ctgggctgta ccttggctcc    1320
ggctacttca ctgccatcca gaacttgagg aaaagtgagg aggaagtggc tgcccggcgt    1380
gcgcgggtcg tgtggtgtgc ggtgggcgag caggagctgc gcaagtgtaa ccagtgggag    1440
ggcttgagcg aaggcagcgt gacctgctcc tcggcctcca ccacagagga ctgcatcgcc    1500

-continued

```
ctggtgctga aggagaagc tgatgccatg agtttggatg gaggatatgt gtacactgca      1560
tgcaaatgtg gtttggtgcc tgtcctggca gagaactaca aatcccaaca aagcagtgac      1620
cctgatccta actgtgtgga tagacctgtg gaaggatatc ttgctgtggc ggtggttagg      1680
agatcagaca ctagccttac ctggaactct gtgaaaggca agaagtcctg ccacaccgcc      1740
gtggacagga ctgcaggctg aatatcccc atgggcctgc tcttcaacca gacgggctcc       1800
tgcaaatttg atgaatattt cagtcaaagc tgtgcccctg ggtctgaccc agatctaat       1860 ctctgtgctc tgtgtattgg cgacgagcag ggtgagaata agtgcgtgcc caacagcaac      1920
gagagatact acggctacac tggggctttc cggtgcctgg ctgagaatgc tggagacgtt      1980
gcatttgtga agatgtcac tgtcttgcag aacactgatg gaaataacaa tgaggcatgg        2040
gctaaggatt tgaagctggc agactttgcg ctgctgtgcc tcgatggcaa acggaagcct      2100
gtgactgagg ctagaagctg ccatcttgcc atggccccga atcatgccgt ggtgtctcgg      2160
atggataagg tggaacgcct gaaacaggtg ctgctccacc aacaggctaa atttgggaga      2220
aatggatctg actgcccgga caagttttgc ttattccagt ctgaaaccaa aaaccttctg      2280
ttcaatgaca acactgagtg tctggccaga ctccatggca aaacaacata tgaaaaatat      2340
ttgggaccac agtatgtcgc aggcattact aatctgaaaa agtgctcaac ctccccctc      2400 ctggaagcct gtgaattcct caggaagtaa aaccgaagaa gatggcccag ctccccaaga      2460
aagcctcagc cattcactgc ccccagctct tctccccagg tgtgttgggg ccttggctcc     2520
cctgctgaag gtggggattg cccatccatc tgcttacaat tccctgctgt cgtcttagca     2580
agaagtaaaa tgagaaattt tgttgatatt caaaaaaaa                             2619
```

<210> SEQ ID NO 15
<211> LENGTH: 892
<212> TYPE: DNA
<213> ORGANISM: Homo sapiens
<220> FEATURE:
<223> OTHER INFORMATION: any n or Xaa = unknown

<400> SEQUENCE: 15

```
tcttgaccgg cacacacagc tcgcttcttc actttctttt ccatccactg ccggacccaa       60
gccagccttc cagggagcag ccatgcctta cctctaccgg gccccagggc tcaggcaca       120 cccggttccc aaggacgccc ggatcaccca ctcctcaggc cagarctttg arcaaatgaa      180
gcaggartgc ctgcagarar gcaccctgtt tgaggatgca gacttcccag ccagcaattc      240
ctccctgttc tacagtgaga ggccgcagat cccctttgtg tggaaacgac cargggaaat     300
cgtgaaaaac ccaraattca ttcttggagg ggccaccagg actgatatct gccagggaga      360
gctgggagac tgctggctat tagccgccat cgcctccctt acgcttaatc aaaaagcact      420
ggccagagtc atccccccagg accaaagctt tggccctggt tatgccggga tattccattt      480
ccagttctgg cagcacagtg agtggctgga cgtggtgatc gatgaccgcc tgcccacctt      540
cagggaccgc ttggttttcc tccactctgc gaccacaac garttctgga rgccttgct       600 ggaaaaagcc tacgccaagc taaatgggag ctatgaagct ctgaagggag gcagcgccat      660
cgaggccatg gaagacttca ctgggggtgt ggcagagacc ttccaaacta agaggcccc      720 cgagaacttc tatgagattc tagagaaggc tttgaagana ngctccctgc tgggctgctt      780
cattgatacc agaagtgctg cagaatctga ggcccggacg ccgtttggtc ttattaaggg      840
tcatgcctac agtgtaacgg gaattgacca ggtaagcttc cgaggccaga ga             892
```

<210> SEQ ID NO 16
<211> LENGTH: 508
<212> TYPE: DNA
<213> ORGANISM: Homo sapiens
<220> FEATURE:
<223> OTHER INFORMATION: any n or Xaa = unknown

<400> SEQUENCE: 16

```
tggagaatgc gagccgggtg ttccaggctc tcagtacaaa gaacanggag ttcattcatn      60
tcaatataaa ngagttcatc cattngacaa tgaacatctg aggctgcntt gtagagatgc     120
agcctgccca gntgatctg ggnttctgga cctngacctt cagaanttct cttggtgtgg     180
aaccattacg cccagggttc actcccctct catcgtccgg ccttctccct tcatcttgat    240
ctgggaagaa tgaaatgaac tcagctacac tctctgattt tgtgctactc ctttgtaaag    300
tcactgcctt aaggggggctg atggcgccac ctgtgcctta catccaggtt caggcatcac    360
tagctttccc acactctact ttccttattt ccttccatta agaattactc agagttctaa    420
cgcacagaat cctgacttcc atgtagctcc agtcattgtg atcagacatc ctttataaaa    480
catgttttta taaatgtgta tgtggaat                                        508
```

<210> SEQ ID NO 17
<211> LENGTH: 194
<212> TYPE: PRT
<213> ORGANISM: Homo sapiens
<220> FEATURE:
<223> OTHER INFORMATION: any n or Xaa = unknown

<400> SEQUENCE: 17

```
Ser Val His Cys Phe Arg Glu Asp Lys Met Lys Phe Thr Ile Val Phe
  1               5                  10                  15
Ala Gly Leu Leu Gly Val Phe Leu Ala Pro Ala Leu Ala Asn Tyr Asn
                 20                  25                  30
Ile Asn Val Asn Asp Asp Asn Asn Ala Gly Ser Gly Gln Gln Ser
             35                  40                  45
Val Ser Val Asn Asn Glu His Asn Val Ala Asn Val Asp Asn Asn Asn
 50                  55                  60
Gly Trp Asp Ser Trp Asn Ser Ile Trp Asp Tyr Gly Asn Gly Phe Ala
 65                  70                  75                  80
Ala Thr Arg Leu Phe Gln Lys Lys Thr Cys Ile Val His Lys Met Asn
                 85                  90                  95
Lys Glu Val Met Pro Ser Ile Gln Ser Leu Asp Ala Leu Val Lys Glu
                100                 105                 110
Lys Lys Leu Gln Gly Lys Gly Pro Gly Pro Pro Lys Gly Leu
            115                 120                 125
Met Tyr Ser Val Asn Pro Asn Lys Val Asp Asp Leu Ser Lys Phe Gly
            130                 135                 140
Lys Asn Ile Ala Asn Met Cys Arg Gly Ile Pro Thr Tyr Met Ala Glu
145                 150                 155                 160
Glu Met Gln Glu Ala Ser Leu Phe Phe Tyr Ser Gly Thr Cys Tyr Thr
                165                 170                 175
Thr Ser Val Leu Trp Ile Val Asp Ile Ser Phe Cys Gly Asp Thr Val
            180                 185                 190

Glu Asn
```

<210> SEQ ID NO 18
<211> LENGTH: 51
<212> TYPE: PRT

```
<213> ORGANISM: Homo sapiens
<220> FEATURE:
<223> OTHER INFORMATION: any n or Xaa = unknown

<400> SEQUENCE: 18

Met Val Asp Asp Lys Arg Lys Ser Ala Leu Trp Lys Glu Arg Thr Val
 1               5                  10                  15

Ser Thr Arg Val Lys Ser Met Asn Ala Ser Ile Glu Arg Thr Arg Gly
             20                  25                  30

Asn Ile Pro Ser Thr Gly Leu His Thr Cys Ile Tyr Ile Leu Glu Asn
         35                  40                  45

Thr Ala Met
     50

<210> SEQ ID NO 19
<211> LENGTH: 63
<212> TYPE: PRT
<213> ORGANISM: Homo sapiens
<220> FEATURE:
<223> OTHER INFORMATION: any n or Xaa = unknown

<400> SEQUENCE: 19

Met Gly Gln Gln His Gln Tyr Tyr Leu Gly Ala Tyr Arg Asn Ala Glu
 1               5                  10                  15

Phe Gln Ala His Cys Arg Ser Thr Glu Ser Lys Ser Ser Phe Ser Lys
             20                  25                  30

Ile Ser Gln Thr Ile Ser Thr Gly Leu His Pro Phe Tyr Pro Ser Leu
         35                  40                  45

Ala Ile Arg Asp Val Arg Ser Glu Gly Phe Lys Arg Ser Pro Glu
     50                  55                  60

<210> SEQ ID NO 20
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 20
tctttgctgg acttcttgga                                              20

<210> SEQ ID NO 21
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 21
ctttgtttgg gttgactgag                                              20

<210> SEQ ID NO 22
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
```

```
            DNA

<400> SEQUENCE: 22
caccctcatt acatcatcag                                                20

<210> SEQ ID NO 23
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 23
attccttgtg tcttctggta                                                20

<210> SEQ ID NO 24
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 24
cagtcctact tctcctatct c                                              21

<210> SEQ ID NO 25
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 25
atcatagctc agaccatacc t                                              21

<210> SEQ ID NO 26
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 26
gatcctgcag gactacaaat c                                              21

<210> SEQ ID NO 27
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 27
```
gcctatatag aaaaatgaag                                                    20

<210> SEQ ID NO 28
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 28
cacctagtga ccgttccaga t                                                  21

<210> SEQ ID NO 29
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 29
ttcatctcct tgggtgttat t                                                  21

<210> SEQ ID NO 30
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 30
ctcagacgct caggaaatag a                                                  21

<210> SEQ ID NO 31
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 31
aatgggggaa gtatgtagga g                                                  21

<210> SEQ ID NO 32
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 32
ttacggatca tttctctact c                                                  21

<210> SEQ ID NO 33

```
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 33
agggcaagat gaagtgaaag g                                              21

<210> SEQ ID NO 34
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 34
tccggaaaga agagcgagag a                                              21

<210> SEQ ID NO 35
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 35
tgaaacacaa ctaccccaat g                                              21

<210> SEQ ID NO 36
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 36
atagcaaagg taaactctca                                                20

<210> SEQ ID NO 37
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 37
tcaatcagta gttcccagta                                                20

<210> SEQ ID NO 38
<211> LENGTH: 20
<212> TYPE: DNA
<213> ORGANISM: Artificial Sequence
<220> FEATURE:
```

```
<223> OTHER INFORMATION: any n or Xaa = unknown
<220> FEATURE:
<223> OTHER INFORMATION: Description of Artificial Sequence: Synthetic
      DNA

<400> SEQUENCE: 38
ttaacagccc aatatctaca                                              20

<210> SEQ ID NO 39
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 39
gaacaagtga ttatgctacc                                              20

<210> SEQ ID NO 40
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 40
agaataagca acttggaaaa                                              20

<210> SEQ ID NO 41
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 41
tgaatctgat gactatgtgc                                              20

<210> SEQ ID NO 42
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 42
tcctggatac cttttggacc                                              20

<210> SEQ ID NO 43
<211> LENGTH: 19
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA
```

```
<400> SEQUENCE: 43
catcagggct acaaggaaa                                              19

<210> SEQ ID NO 44
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 44
cagatctacc gaatcaaaat c                                           21

<210> SEQ ID NO 45
<211> LENGTH: 21
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 45
accagaatta ggaataagga t                                           21

<210> SEQ ID NO 46
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 46
gactccatgg caaaacaaca                                             20

<210> SEQ ID NO 47
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 47
tcttcttcgg ttttacttcc                                             20

<210> SEQ ID NO 48
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 48
aggcaccagg gcgtgatggt                                             20
```

<210> SEQ ID NO 49
<211> LENGTH: 20
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 49
ggtctcaaac atgatctggg                                              20

<210> SEQ ID NO 50
<211> LENGTH: 10
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 50
cttgattgcc                                                         10

<210> SEQ ID NO 51
<211> LENGTH: 10
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 51
aggtgaccgt                                                         10

<210> SEQ ID NO 52
<211> LENGTH: 10
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 52
gttgcgatcc                                                         10

<210> SEQ ID NO 53
<211> LENGTH: 10
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 53
ctgatccatg                                                         10

<210> SEQ ID NO 54
<211> LENGTH: 10

```
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 54
ctgcttgatg                                                          10

<210> SEQ ID NO 55
<211> LENGTH: 10
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 55
gatctgactg                                                          10

<210> SEQ ID NO 56
<211> LENGTH: 13
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 56
tttttttttt taa                                                      13

<210> SEQ ID NO 57
<211> LENGTH: 13
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 57
tttttttttt tac                                                      13

<210> SEQ ID NO 58
<211> LENGTH: 13
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 58
tttttttttt tag                                                      13

<210> SEQ ID NO 59
<211> LENGTH: 13
<212> TYPE: DNA
<213> ORGANISM: Artificial Sequence
<220> FEATURE:
<223> OTHER INFORMATION: any n or Xaa = unknown
```

```
<220> FEATURE:
<223> OTHER INFORMATION: Description of Artificial Sequence: Synthetic
      DNA

<400> SEQUENCE: 59
tttttttttt tca                                                          13

<210> SEQ ID NO 60
<211> LENGTH: 13
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 60
tttttttttt tcc                                                          13

<210> SEQ ID NO 61
<211> LENGTH: 13
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 61
tttttttttt tcg                                                          13

<210> SEQ ID NO 62
<211> LENGTH: 13
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 62
tttttttttt tga                                                          13

<210> SEQ ID NO 63
<211> LENGTH: 13
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 63
tttttttttt tgc                                                          13

<210> SEQ ID NO 64
<211> LENGTH: 13
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA
```

<400> SEQUENCE: 64
tttttttttt tgg                                                    13

<210> SEQ ID NO 65
<211> LENGTH: 264
<212> TYPE: DNA
<213> ORGANISM: Artificial Sequence
<220> FEATURE:
<223> OTHER INFORMATION: any n or Xaa = unknown
<220> FEATURE:
<223> OTHER INFORMATION: Description of Artificial Sequence: Synthetic
      DNA

<400> SEQUENCE: 65
aggcaccagg gcgtgatggt gggcatgggt cagaaggatt cctatgtggg cgacgaggcc    60
cagagcaaga gaggcatcct caccctgaag tacccatcg agcacggcat cgtcaccaac    120
tgggacgaca tggagaaaat ctggcaccac accttctaca atgagctgcg tgtggctccc    180
gaggagcacc ccgtgctgct gaccgaggcc cccctgaacc ccaaggccaa ccgcgagaag    240
atgacccaga tcatgtttga gacc                                          264

<210> SEQ ID NO 66
<211> LENGTH: 814
<212> TYPE: DNA
<213> ORGANISM: Homo sapiens
<220> FEATURE:
<223> OTHER INFORMATION: any n or Xaa = unknown

<400> SEQUENCE: 66
ataacaccta gtttgagtca acctggttaa gtacaaatat gagaaggctt ctcattcagg    60
tccatgcttg cctactcctc tgtccactgc tttcgtgaag acaagatgaa gttcacaatt    120
gtctttgctg gacttcttgg agtctttcta gctcctgccc ttgctaacta taatatcaac    180
gtcaatgatg acaacaacaa tgctggaagt gggcagcagt cagtgagtgt caacaatgaa    240
cacaatgtgg ccaatgttga caataacaac ggatgggact cctggaattc catctgggat    300
tatggaaatg gctttgctgc aaccagactc tttcaaaaga gacatgcat tgtgcacaaa    360 atgaacaagg aagtcatgcc ctccattcaa tcccttgatg cactggtcaa ggaaaagaag    420
cttcagggta agggaccagg aggaccacct cccaagggcc tgatgtactc agtcaaccca    480
aacaaagtcg atgacctgag caagttcgga aaaaacattg caaacatgtg tcgtgggatt    540
ccaacataca tggctgagga gatgcaagag gcaagcctgt ttttttactc aggaacgtgc    600
tacacgacca gtgtactatg gattgtggac atttccttct gtggagacac ggtggagaac    660
taaacaattt tttaaagcca ctatggattt agtcgtctga atatgctgtg cagaaaaaat    720
atgggctcca gtggttttta ccatgtcatt ctgaaatttt tctctactag ttatgtttga    780 tttcttaag tttcaataaa atcatttagc attg                               814

<210> SEQ ID NO 67
<211> LENGTH: 4646
<212> TYPE: DNA
<213> ORGANISM: Homo sapiens
<220> FEATURE:
<223> OTHER INFORMATION: any n or Xaa = unknown

<400> SEQUENCE: 67
tatgtgccag gtgctctgtt gggtgccaag tgaaatgcaa ataaatggga acagtactca    60
gttcagtttg ctttgggaat taattacatg ccatgtgtgt aaattgtgct aaattttagg   120

-continued

```
aatacagaaa tgaattaaac gtctccaggg aacacatagt ctagtgaaga agctgacaag    180
tgaaaagaga ggatggagta aaggatttct ggatgccaat gaaaaactac tcgattcttg    240
tatactttca tatgtaagaa tttcaagtag caaaaagtca tctgggccct tagaatagca    300
tattttgaag ataataagaa ggaagtcact aagaaatgct ctcaggatct agaatagaat    360
tggtatagga agaggaggc caagcggact tacagacagg gagtaaaaac cctgattcat     420
ctgggtaaca tatgccactg cagatattac tgtcattttt atacaaagtt tctaaatgtg    480
gcagagcaac cagagtgaaa gaggtcgggc caactgatga tgaacacaac aaaggaaatt    540
tctcagagta ctggaaggta gataaagaag agtttatgtt tattatatat ctactgccca    600
gaaaaaaatt ttaagtactc attcataaag taaataaagg cataggta tgccattgac      660 acagaatggc ataatatcac tgggattgag ccaaccagca cttccaaaag ttgtcagttt    720
tatttaagct aatgtattat tattctaata attccaataa tatattttt aatgctcttt     780 ctctgaaaaa ttttcccttt tccagataat gtcggtgctg gaggctgtgc aaaggctggg    840
ctcctgggca tcttgggaat ttcaatctgt gcagacattc atgtttagga tgattagccc    900
tcttgtttta tcttttcaaa gaaatacatc cttggtttac actcaaaagt caaattaaat    960
tctttcccaa tgccccaact aattttgaga ttcagtcaga aaatataaat gctgtatttta   1020 tagatttttt ggtgtntgtt gttttttgta agcagcaaag ggaatccaag caatgtcttt    1080
gtcactatat agaataaaaa aaattgccag aattttaaat aaggtgcata atgtgtgaaa    1140
attcccagat aataccactg ggtcacatgt ggactagtca gctgggtcg aatttccatt     1200 tcttcgtntg ccctctggac cagcttccca tctaaccatc caaatatatg ggagcaacct    1260
gggtagagaa gaggctcaca cggtggtggc cttgacctgg ccaggggagg acatagcgt     1320 atgcttatca aacaagttga atgctcaggt gaaggctttt agggccattc atatgagtta    1380
aaatgtcctt taactcacca aagcagtaga ctcaacctga ataaacttta taataatatg    1440
tgttgccctg gagtgagaag ggagaaaggg agagaggaag gagcacctaa catccaggaa    1500
aagatgcacc atactgaaga tcataacagg agtgaaagac tagaaatgcc aagtcaatac    1560
atagcagaaa agcaacttcc aatatttcaa ataaattgca cattgtgtac aaatctcaga    1620
tcgtgaagct gggtcacacg tgaacgttcg gctgaatgca aattcagagc aaagaggaat    1680
tactttaata acaatttatt ctcttgccgt agacctctgg gatcctagct gcagaggacc    1740
cccggcctcc gcgtttgagc tgacatgaga ctctcactag agattagatg gagaaagggc    1800
tccagcaggc acggagctgg aagctttgtc tgtgagacag ctccgcggga gcactcatcc    1860
cccagggctc tctgtctccc tctgagaggc tctggcccca tntaaccacc agaatgggag    1920
aagaagtgct tccccgtggg attagggcac atctgtcccg caggcccacc tgcctgccag    1980
tccctcccag gattcctgcc tggccacccc acaggagtgt gtacacagtg cagcctcagc    2040
tgctcagcat gggtgctttg ctccacttga gtgcattccg gcagcgtggg agctgtttga    2100 atccccagt gcacacagat cccaaccccca agggtccagg ggaggagct gtgagcagat     2160 ccggacgtcc cagggctgtg gctccggagt gcggaactgg gcccagtgct tcagcagaag    2220
aggagcccat actctcagaa aactctcaga gaggggtgag tngnacaggt tcctgggctg    2280
gtgtggaacc tangcgtgcc tncctncaca gagctggtcc agtaagtgtg gggcctgtct    2340
ccctgctgga cctctgcctg aaggagccca acgacctgga acacctaaca acaacagaaa   2400
gtcncggcca cagtgccagt gatcagggt ccctcccctc aagaccgagg aggagacctg     2460
gtgaggggtc acccctctcc cccttgcacc acagagcacg gcttcaaagg cccggataca    2520
```

-continued

```
caaaggagcc gggtggcaga atattagtct agctatctcc cattgctctc acgcgccatc    2580
tactggattt catcccaaac tacaacacga aaaactgcta attttcctgc ctgccaggcc    2640
gaggactgga attcaacaga ctgtttagag cctttgccct ctgaaaactt ccagaaatga    2700
agccaactga ctatattcag tttacaccag agttaaagga acgccaaccc tcccagatga    2760
gaaagaatca gtgcaagaac tgtagcaatt taaaaaacca gagcgtcccc ttacctccaa    2820
atgagcccac tagctccaca gcaattgttc ttaaccaatc tgaaatgatg agcatggaat    2880
tcagaatctg aatggcaatg aagcttatag atatccagga gaaagttgaa atgcaatcca    2940
aggaaaccaa gcaatccagt gaaatggttt aagagctgaa agataaaata ncaattttac    3000
aaaagaccca aactgagctt attgagttca aaaaagaatt tcataataca atcagaagta    3060
ttaatagcag aataggccaa gctgaggaaa gaatctcaga gcttgacccc tggttctttg    3120
aatcaactta gacaaaaata aagaaaaaag agttttaaga aatgaacaca atctcccaga    3180
aatatgagat tatgtwaaga gacaaaatct atgactcatt gccatccctg agagagaagg    3240
agagagaata agcaacttgg aaaatatatt tggggacata gccacaaaaa atttccctaa    3300
tctctctaga gaggttgaca tgtaaattca agaaatacag aagaccttgg ccagataata    3360
tacaagatga ccatccccaa ggcacatagt catcagattc accatggtca atgcaaaaga    3420
aaaaaatctt aaagacagct agggagaagg gtcaagtcac atgcagaagg actctcatta    3480
ggctggcagt ggacctctca gcagaaacct gacaagccag aagagatgga gggagagggg    3540 tctattttttg tcatccttaa agaaaaaaaa ttccaaccaa gagtctcata cactgccaaa    3600
ctaagcttcc taagtgaagg agaaataaaa accttctcag acaagcaaat gctgaaggaa    3660
ttcaactaga ccagcctaac aagaggtcct aagggagtgc tgaatatgga ctcaaaagaa    3720
taacacctgc taccaaaac actcacttaa gcacacagcc caacgacact ataggcaatt    3780
acacagtaag tctacataac aacacaatga caggatcaac atctcacaca tcaatactaa    3840
ccccgagtgt aaagggggcta aatgccccac ttaaaagaca tagagtgtca agcttgataa    3900
aaagacaaga tccaatcatc cactatttttc aagagctcta tgttatgtgt aatgacaccc    3960
acagactcaa agacttggag aaagatttat catgcaaaat cagaaaacaa aaaagagcag    4020
gagtcactag ttttatatca gacaaaacag actttaaacc cttaataatt aagaaagaca    4080
aagaagggta tttcctggac cacagaaggc ttattggaaa aaaggacata atgacaaagg    4140
gtacaatcca acaagaagtt ttaactattc taaatatata cacacccaac attggagcac    4200
ccagatttat aaaacaagta cttctcgatc tacaagaaga cttagacagc cacacaataa    4260
tagtgggaga ctttcacatc ctacttacag atcattgaga cagaaaacta ataaagaac    4320 tctggactta aacttgttac ttgaccaatt ggacctaata gatatccaca gaaaacttca    4380
cccaacaaag acagaatata cattcttctt atctgcacat ggaacacatt ccaagatcaa    4440
tcacatgcta ggtaagaaag caagtctcaa taaattaaaa aaaattgaaa tcatacgaac    4500
cttaatatca gaccacaatg taattaaaaa taaatcaata tcaagaagat ctcatacata    4560
aatacatgaa aattaaacaa cttactcctg aataactctt gtgtgaacat caaaattcag    4620
gaagaaataa aaaattattt gaaatt                                          4646
```

<210> SEQ ID NO 68
<211> LENGTH: 2484
<212> TYPE: DNA
<213> ORGANISM: Homo sapiens
<220> FEATURE:

<223> OTHER INFORMATION: any n or Xaa = unknown

<400> SEQUENCE: 68

```
tcttgaccgg cacacacagc tcgcttcttc actttctttt ccatccactg ccggacccaa      60
gccagccttc cagggagcag ccatgcctta cctctaccgg ccccagggc ctcaggcaca      120
cccggttccc aaggacgccc ggatcaccca ctcctcaggc cagagctttg agcaaatgag      180
gcaggagtgc ctgcagagag gcaccctgtt tgaggatgca gacttccag ccagcaattc      240
ctccctgttc tacagtgaga ggccgcagat ccccttttgtg tggaaacgac caggggaaat      300
cgtgaaaaac ccagaattca ttcttggagg ggccaccagg actgatatct gccagggaga      360
gctgggagac tgctggctat tagccgccat cgcctccctt acgcttaatc aaaaagcact      420
ggccagagtc atcccccagg accaaagctt tggccctggt tatgccggga tattccattt      480
ccagttctgg cagcacagtg agtggctgga cgtggtgatc gatgaccgcc tgcccaccct      540
cagggaccgc ttggttttcc tccactctgc cgaccacaac gagttctgga gcgccttgct      600
ggaaaaagcc tacgccaagc taatgggag ctatgaagct ctgaaggag gcagcgccat      660
cgaggccatg aagacttca ctgggggtgt ggcagagacc ttccaaacta agaggcccc      720
cgagaacttc tatgagattc tagagaaggc tttgaagaga ggctccctgc tgggctgctt      780
cattgatacc agaagtgctg cagaatctga ggcccggacg ccgtttggtc ttattaaggg      840
tcatgcctac agtgtaacgg gaattgacca ggtaagcttc cgaggccaga gaatcgagct      900
catccgaatc cggaaccctt ggggccaggt tgagtggaac gggtcgtgga gcgacaggat      960
ggcatttaag gacttcaagg cccactttga taaagtggag atctgcaacc tcactcccga      1020
tgccctggag gaagacgcga tccacaaatg ggaggtgacg gtccatcagg gaagctgggt      1080
tcgcggctcc acggctgggg gctgccgcaa tttcctggat accttttgga ccaatccaca      1140
aataaaattg tctctgactg agaaagatga ggggcaggag gagtgtagtt tccttgtagc      1200
cctgatgcag aaagatagaa ggaaactcaa gagatttggt gccaatgtgc tgacaatcgg      1260
ctatgccatt tatgagtgcc ctgacaaaga cgaacacctg aacaaagact tcttcagata      1320
ccacgcttct cgggccagaa gcaagacgtt catcaacctg agagaagtct ccgaccggtt      1380
caagctgccc cctggggagt acatcctgat tcccagcact tttgagcccc accaggaagc      1440
tgatttctgt ctgagaatct tttcagagaa aaaagccatt acccgggata tggatggaaa      1500
tgtagacatt gaccttcctg agcctccaaa gccaactcca cctgaccagg agacagagga      1560
ggagcagcgg tttcgggctc tgtttgaaca agtcgctggt gaggacatgg aggtgacagc      1620
agaggaactt gagtatgttt taaatgctgt gctgcaaaag aaaaaggaca tcaaattcaa      1680
gaagctaagc ctgatctcct gtaaaaacat catttccctg atggacacca gcggcaatgg      1740
gaagctggag tttgatgaat tcaaagtgtt ctgggacaag ctgaagcagt ggattaacct      1800
tttccttcgg tttgatgctg acaagtccgg caccatgtct acctatgaac tacggactgc      1860
actgaaagct gcaggctttc agctgagcag ccacctcctg cagctgattg tgctcaggta      1920
tgcggatgag gagctccagc tggacttcga tgacttcctc aactgcctgg tccggctgga      1980
gaatgcgagc cgggtgttcc aggctctcag tacaaagaac aaggagttca ttcatctcaa      2040
tataaatgag ttcatccatt tgacaatgaa catctgaggc tgccttgtag agatgcagcc      2100
tgcccagctg aatcttggct tctgaccctt gaccttcaga acttctcttg gtgtggaacc      2160
attacgccca gggttcactc ccctctcatc gtccggcctt ctcccttcat cttgatctgg      2220
gaagaatgaa atgaactcag ctacactctc tgattttgtg ctactccttt gtaaagtcac      2280
```

-continued

```
tgccttaagg gggctgatgg cgccacctgt gccttacatc caggttcagg catcactagc    2340
tttcccacac tctactttcc ttatttcctt ccattaagaa ttactcagag ttctaacgca    2400
cagaatcctg acttccatgt agctccagtc attgtgatca gacatccttt ataaacatg     2460 tttttataaa tgtgtatgtg gaat                                            2484
```

<210> SEQ ID NO 69
<211> LENGTH: 199
<212> TYPE: PRT
<213> ORGANISM: Homo sapiens
<220> FEATURE:
<223> OTHER INFORMATION: any n or Xaa = unknown

<400> SEQUENCE: 69

Met Leu Ala Tyr Ser Ser Val His Cys Phe Arg Glu Asp Lys Met Lys
 1               5                  10                  15

Phe Thr Ile Val Phe Ala Gly Leu Leu Gly Val Phe Leu Ala Pro Ala
             20                  25                  30

Leu Ala Asn Tyr Asn Ile Asn Val Asn Asp Asp Asn Asn Asn Ala Gly
         35                  40                  45

Ser Gly Gln Gln Ser Val Ser Val Asn Asn Glu His Asn Val Ala Asn
     50                  55                  60

Val Asp Asn Asn Asn Gly Trp Asp Ser Trp Asn Ser Ile Trp Asp Tyr
 65                  70                  75                  80

Gly Asn Gly Phe Ala Ala Thr Arg Leu Phe Gln Lys Lys Thr Cys Ile
                 85                  90                  95

Val His Lys Met Asn Lys Glu Val Met Pro Ser Ile Gln Ser Leu Asp
            100                 105                 110

Ala Leu Val Lys Glu Lys Lys Leu Gln Gly Lys Gly Pro Gly Gly Pro
        115                 120                 125

Pro Pro Lys Gly Leu Met Tyr Ser Val Asn Pro Asn Lys Val Asp Asp
    130                 135                 140

Leu Ser Lys Phe Gly Lys Asn Ile Ala Asn Met Cys Arg Gly Ile Pro
145                 150                 155                 160

Thr Tyr Met Ala Glu Glu Met Gln Glu Ala Ser Leu Phe Phe Tyr Ser
                165                 170                 175

Gly Thr Cys Tyr Thr Thr Ser Val Leu Trp Ile Val Asp Ile Ser Phe
            180                 185                 190

Cys Gly Asp Thr Val Glu Asn
        195

<210> SEQ ID NO 70
<211> LENGTH: 664
<212> TYPE: PRT
<213> ORGANISM: Homo sapiens
<220> FEATURE:
<223> OTHER INFORMATION: any n or Xaa = unknown

<400> SEQUENCE: 70

Met Pro Tyr Leu Tyr Arg Ala Pro Gly Pro Gln Ala His Pro Val Pro
 1               5                  10                  15

Lys Asp Ala Arg Ile Thr His Ser Ser Gly Gln Ser Phe Glu Gln Met
             20                  25                  30

Arg Gln Glu Cys Leu Gln Arg Gly Thr Leu Phe Glu Asp Ala Asp Phe
         35                  40                  45

Pro Ala Ser Asn Ser Ser Leu Phe Tyr Ser Glu Arg Pro Gln Ile Pro
     50                  55                  60

-continued

```
Phe Val Trp Lys Arg Pro Gly Glu Ile Val Lys Asn Pro Glu Phe Ile
 65                  70                  75                  80

Leu Gly Gly Ala Thr Arg Thr Asp Ile Cys Gln Gly Glu Leu Gly Asp
                 85                  90                  95

Cys Trp Leu Leu Ala Ala Ile Ala Ser Leu Thr Leu Asn Gln Lys Ala
            100                 105                 110

Leu Ala Arg Val Ile Pro Gln Asp Gln Ser Phe Gly Pro Gly Tyr Ala
            115                 120                 125

Gly Ile Phe His Phe Gln Phe Trp Gln His Ser Glu Trp Leu Asp Val
130                 135                 140

Val Ile Asp Asp Arg Leu Pro Thr Phe Arg Asp Arg Leu Val Phe Leu
145                 150                 155                 160

His Ser Ala Asp His Asn Glu Phe Trp Ser Ala Leu Leu Glu Lys Ala
                165                 170                 175

Tyr Ala Lys Leu Asn Gly Ser Tyr Glu Ala Leu Lys Gly Gly Ser Ala
            180                 185                 190

Ile Glu Ala Met Glu Asp Phe Thr Gly Gly Val Ala Glu Thr Phe Gln
            195                 200                 205

Thr Lys Glu Ala Pro Glu Asn Phe Tyr Glu Ile Leu Glu Lys Ala Leu
            210                 215                 220

Lys Arg Gly Ser Leu Leu Gly Cys Phe Ile Asp Thr Arg Ser Ala Ala
225                 230                 235                 240

Glu Ser Glu Ala Arg Thr Pro Phe Gly Leu Ile Lys Gly His Ala Tyr
                245                 250                 255

Ser Val Thr Gly Ile Asp Gln Val Ser Phe Arg Gly Gln Arg Ile Glu
            260                 265                 270

Leu Ile Arg Ile Arg Asn Pro Trp Gly Gln Val Glu Trp Asn Gly Ser
            275                 280                 285

Trp Ser Asp Arg Met Ala Phe Lys Asp Phe Lys Ala His Phe Asp Lys
            290                 295                 300

Val Glu Ile Cys Asn Leu Thr Pro Asp Ala Leu Glu Glu Asp Ala Ile
305                 310                 315                 320

His Lys Trp Glu Val Thr Val His Gln Gly Ser Trp Val Arg Gly Ser
                325                 330                 335

Thr Ala Gly Gly Cys Arg Asn Phe Leu Asp Thr Phe Trp Thr Asn Pro
            340                 345                 350

Gln Ile Lys Leu Ser Leu Thr Glu Lys Asp Glu Gly Gln Glu Glu Cys
            355                 360                 365

Ser Phe Leu Val Ala Leu Met Gln Lys Asp Arg Arg Lys Leu Lys Arg
370                 375                 380

Phe Gly Ala Asn Val Leu Thr Ile Gly Tyr Ala Ile Tyr Glu Cys Pro
385                 390                 395                 400

Asp Lys Asp Glu His Leu Asn Lys Asp Phe Phe Arg Tyr His Ala Ser
                405                 410                 415

Arg Ala Arg Ser Lys Thr Phe Ile Asn Leu Arg Glu Val Ser Asp Arg
            420                 425                 430

Phe Lys Leu Pro Pro Gly Glu Tyr Ile Leu Ile Pro Ser Thr Phe Glu
            435                 440                 445

Pro His Gln Glu Ala Asp Phe Cys Leu Arg Ile Phe Ser Glu Lys Lys
            450                 455                 460

Ala Ile Thr Arg Asp Met Asp Gly Asn Val Asp Ile Asp Leu Pro Glu
465                 470                 475                 480
```

```
Pro Pro Lys Pro Thr Pro Pro Asp Gln Glu Thr Glu Glu Gln Arg
            485             490              495

Phe Arg Ala Leu Phe Glu Gln Val Ala Gly Glu Asp Met Glu Val Thr
            500             505              510

Ala Glu Glu Leu Glu Tyr Val Leu Asn Ala Val Leu Gln Lys Lys Lys
        515             520              525

Asp Ile Lys Phe Lys Lys Leu Ser Leu Ile Ser Cys Lys Asn Ile Ile
        530             535             540

Ser Leu Met Asp Thr Ser Gly Asn Gly Lys Leu Glu Phe Asp Glu Phe
545             550             555                     560

Lys Val Phe Trp Asp Lys Leu Lys Gln Trp Ile Asn Leu Phe Leu Arg
            565             570             575

Phe Asp Ala Asp Lys Ser Gly Thr Met Ser Thr Tyr Glu Leu Arg Thr
            580             585             590

Ala Leu Lys Ala Ala Gly Phe Gln Leu Ser Ser His Leu Leu Gln Leu
        595             600             605

Ile Val Leu Arg Tyr Ala Asp Glu Glu Leu Gln Leu Asp Phe Asp Asp
        610             615             620

Phe Leu Asn Cys Leu Val Arg Leu Glu Asn Ala Ser Arg Val Phe Gln
625             630             635                     640

Ala Leu Ser Thr Lys Asn Lys Glu Phe Ile His Leu Asn Ile Asn Glu
            645             650             655

Phe Ile His Leu Thr Met Asn Ile
            660
```